(12) United States Patent
Wang et al.

(10) Patent No.: US 6,468,785 B1
(45) Date of Patent: *Oct. 22, 2002

(54) DOPED CONDUCTING POLYMERS APPLICATIONS AND METHODS

(75) Inventors: Joseph Wang; Mian Jiang, both of Las Cruces, NM (US); Baidehi Mukherjee, Binghamton, NY (US); Antonio Fortes, Minneapolis, MN (US)

(73) Assignee: New Mexico State University Technology Transfer Corporation, Las Cruces, NM (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/507,387

(22) Filed: Feb. 18, 2000

Related U.S. Application Data

(60) Provisional application No. 60/120,778, filed on Feb. 19, 1999, and provisional application No. 60/131,786, filed on Apr. 30, 1999.

(51) Int. Cl.[7] ............................. C12M 1/34; C12Q 1/68; C12P 19/34; C07H 21/02; C07H 21/04
(52) U.S. Cl. ...................... 435/287.2; 435/6; 435/91.1; 435/287.1; 536/23.1; 536/24.3
(58) Field of Search .................. 435/6, 91.1, 91.2, 435/183, 283.1, 287.1, 287.2; 436/94; 536/23.1, 24.3, 24.33, 25.3

(56) References Cited

U.S. PATENT DOCUMENTS

| | | |
|---|---|---|
| 5,156,810 A | 10/1992 | Ribi et al. |
| 5,192,416 A | 3/1993 | Wang et al. |
| 5,292,423 A | 3/1994 | Wang |
| 5,516,644 A | 5/1996 | Yamauchi et al. |
| 5,676,820 A | 10/1997 | Wang |
| 5,776,672 A | 7/1998 | Hashimoto et al. |
| 5,837,859 A | 11/1998 | Teoule et al. |
| 5,942,103 A | 8/1999 | Wang et al. |
| 5,952,172 A * | 9/1999 | Meade et al. .................. 435/6 |
| 6,063,259 A | 5/2000 | Wang et al. |
| 6,071,699 A * | 6/2000 | Meade et al. .................. 435/6 |
| 6,087,100 A * | 7/2000 | Meade et al. .................. 435/6 |

FOREIGN PATENT DOCUMENTS

| | | |
|---|---|---|
| WO | WO95/19199 | 11/1995 |
| WO | WO99/18242 | 4/1999 |

OTHER PUBLICATIONS

Barisci et al., Characterization and analytical use of polypyrrole electrode containing anti–human serum albumin. Anal. Chim. Acta, 371, 39–48, Sep., 1998.*

Sadik et al., Pulsed amerometric detection of proteins using antibody containing conducting polymers. Anal. Chim. Acta, 279, 209–212, 1993.*

Napier et al., Probing biomolecule recognition with electron transfer: electrochemical sensors for DNA hybridization. Bioconjugate Chem., 906–913, Nov. 1997).*

Wang et al., Trace measurements of nucleic acids using flow injection amperometry. Anal. Chim. Acta 319, 347–352, 1996.*

(List continued on next page.)

*Primary Examiner*—Ethan C. Whisenant
*Assistant Examiner*—Frank Lu
(74) *Attorney, Agent, or Firm*—Stephen A. Slusher; Nancy E. Ownbey

(57) ABSTRACT

An apparatus for electrochemical detection of DNA hybridization utilizing oligonucleotide-containing polymer-coated electrodes, and an apparatus for electrochemical detection of nucleic acids in flowing streams using doped polymer-coated electrodes. Also provided are methods for detection of DNA hybridization and for detection of nucleic acids in flowing streams.

24 Claims, 11 Drawing Sheets

OTHER PUBLICATIONS

Livache et al., Biosensing effects in functionalized electro-conducting conjugated polymer layers: addressable DNA matrix for the detection of gene mutations. Synthetic Metals 71, 2143–2146, 1995.*

Livache et al., Preparation of DNA matrix via an electrochemically directed copolymerization of pyrrole and oligonucleotides bearing a pyrrole group. Nucleic Acids Res. 22. 2915–2921, 1994.*

Korri–Yousoufi et al., Toward Bioelectronics: Specific DNA recognition based on an oligonucleotide–functionalized polypyrrole. J. Am. Chen. Soc. 119, 7388–7389, 1997.*

Korri–Youssoufi, H., et al., "Toward Bioelectronics specific DNA Recognition Based on an Oligonucleotide–Functionalized Polyyprrole," *J. Am. chem. Soc.*, vol. 119, pp 7388–7389 (1997).

Wang, J., et al., "New Label–Free DNA Recognition Bsed on Doping Nucleic–Acid Probes Within Conducting Polymer Films," *Analytica Chimica Acta*, vol. 402, pp 7–12 (1999).

Wang, J., et al., "Flow Detection of Nucleic Acids at a Conducting Polymer-Modified Electrode," *Analytical Chem.*, vol. 71, No. 18, pp 4095–4099 (1999).

Wang, J., owards Genoelectronics: Electrochemical Biosensing of DNA Hybridization, *Chem. Eur. J.*, vol. 5, No. 6, pp 1681–1684 (1999).

Bauerle, P., et al., "Specific Recognition of Nucleobase–Funcionalized Polytiopenes," *Adv. Mater.*, vol. 3, No. 4, pp 324–331 (1998).

Hashimoto, K., et al., "Sequence–Specific Gene Detection with a Gold Electrode Modified with DNA Probes and an Electrochemically Active Dye," *Anal. Chem.*, vol. 66, pp 3830–3833 (1994).

Mikkelsen, S.R., "Electrochemical Biosensors for DNA Sequence Detection," *Electoanalysis*, vol. 8, No. 1, pp 15–19 (1996).

Millan, K.M., et al., "Sequence–Selective Biosensor for DNA Based on Electroactive Hybridization Indicators," *Anal. Chem.*, vol. 65, pp 2317–2323 (1993).

Singhal, P., et al., "Ultrasensitive Voltammetric Detection of Underivated Oligonucleotides and DNA," *Anal Chem.*, vol. 69, pp 4828–4832 (1997).

Takenaka, S., et al., "Electrochemically Active DNA Probes: Detection of Target DNA Sequences at Femtomole Level by High–Performance Liquid Chromatography with Electrochemical Detection," *Analytical Biochemistry*, vol. 218 pp 436–443 (1994).

Wang, J., et al., "Indicator–Free Electrochemicl DNA Hybridization Biosensor," *Anal Chim. Acta*, vol. 375, pp 197–203 (1998).

Wang, J., et al., "Electrochemical Biosensor for Detection DNA Sequences from the Pathogenic Protozan *Cryptosporidium parvum*," *Talanta* vol. 44, pp 2003–2010 (1997).

Wang, J., et al., "Trace Measurements of Nucleic Acids Using Flow Injection Amperometry," *Anal. Chim Acta*, vol. 317, pp 347–352 (1996).

Wang, et al., TEXTBOOK "Analytical Electrochemistry," VCH Publishers, New York, pp 92–95 "Conducting Polymers," (1994).

Wilson, E.K., "Instant DNA Detection," *Chem. Eng. News.*, May 25, 1998 pp 47–49.

Woolley A.T., et al., "Capillary Electrophoresis Chips with Integrated Electrochemical Detection," *Anal. Chem.*, vol 70, pp684–688 (1998).

Xu, D–K., et al., "Determination of Purine Bases by Capillary Zone Electrophoresis with Wall–Jet Amperometric Detection," *Anal. Chim. Acta*, vol. 335, pp 95–101 (1996).

* cited by examiner

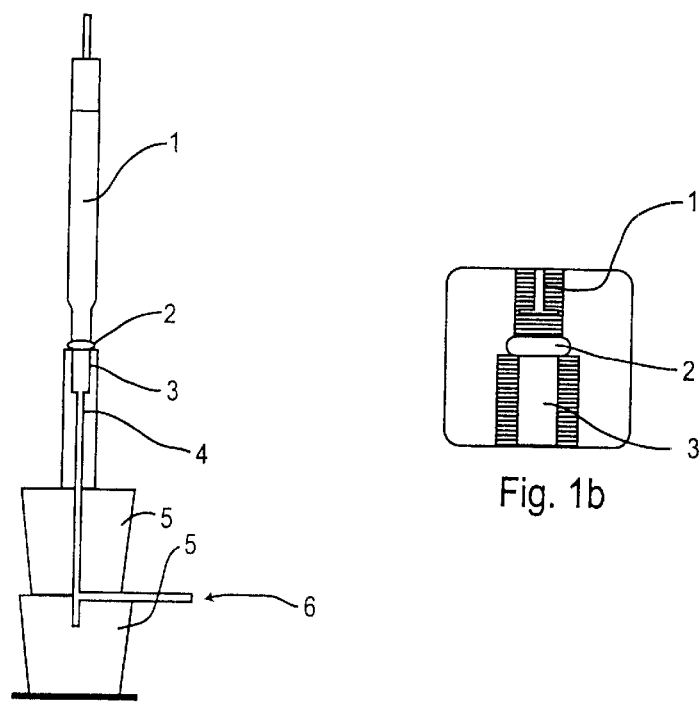
Fig. 1b
Fig. 1a
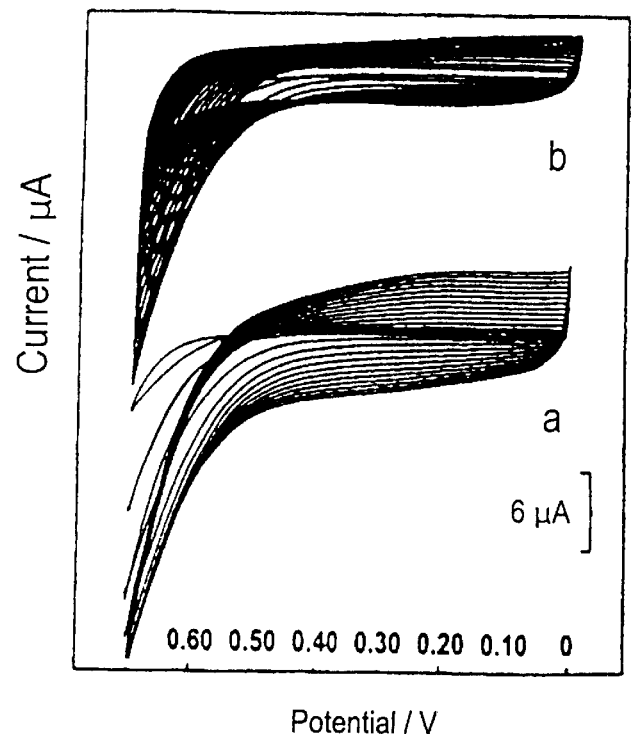
Fig. 2

SEQUENCE LISTING

```
<160> NUMBER OF SEQ ID NOS: 2

<210> SEQ ID NO 1
<211> LENGTH: 25
<212> TYPE: DNA
<213> ORGANISM: Escherichia coli

<400> SEQUENCE: 1
tgccgctcat ccgccacata tcctg                                             25

<210> SEQ ID NO 2
<211> LENGTH: 12
<212> TYPE: DNA
<213> ORGANISM: Unknown
<220> FEATURE:
<223> OTHER INFORMATION: Description of Unknown Organism:Test
      oligonucleotide

<400> SEQUENCE: 2
agagagagag ag                                                           12
```

DOPED CONDUCTING POLYMERS APPLICATIONS AND METHODS

CROSS-REFERENCE TO RELATED APPLICATIONS

This application claims the benefit of the filing of U.S. Provisional Patent Application Ser. No. 60/120,778, entitled "Genoelectronics: Direct Electrical Detection of DNA Hybridization Based on Doping Nucleic Acid Probes within Conducting-Polymer Films," filed on Feb. 19, 1999, and U.S. Provisional Patent Application Ser. No. 60/131,786, entitled "Flow Detection of Nucleic Acids at Conducting-Polymer Modified Electrode," filed on Apr. 30, 1999, the specifications of both of which are incorporated herein by reference.

GOVERNMENT RIGHTS

The U.S. Government has a paid-up license in this invention and the right in limited circumstances to require the patent owner to license others on reasonable terms as provided for by the terms of Contract No. ROI RR14549-01 awarded by the U.S. National Institutes of Health of the Department of Health and Human Services.

BACKGROUND OF THE INVENTION

1. Field of the Invention (Technical Field)

The present invention relates to methods, compositions and devices for the detection of nucleic acids utilizing electrochemical detection with polymer-coated electrodes.

2. Background Art

The biological significance of nucleic acids has required the development of novel analytical methods for their detection and quantitation. Historical methods involve use of gel electrophoresis with radioactive labeled probes. Other label methods have been used, including biotin, digoxigenin and fluorescent dyes. These methods all involve long detection times and complex laboratory procedures, with ancillary amplification methods, such as polymerase chain reaction (PCR), frequently required to produce sufficient materials for detection.

In some applications, microscale separation techniques such as capillary electrophoresis are coupled to optical detection techniques for identification of individual nucleic acids. UV absorbance and laser-induced fluorescence systems have been used for this purpose. Electrochemical detectors, while used for other bioanalytical applications (Wang, J. Analytical Electrochemistry, VCH Publishers, New York, 1994; U.S. Pat. No. 5,516,644), have received only limited attention for nucleic acid analysis. However, electrochemical detector analysis systems, if demonstrated to be accurate and reproducible, offer potential advantages for detection of DNA and RNA and for "lab-on-a-chip" devices, including high sensitivity and selectivity, ultra-small dead volumes, fast response, compatibility with advanced microfabrication and miniaturization technologies, low-cost, and minimal power requirements.

Electrochemical detection of DNA has traditionally relied on the electroactivity of nucleobases. In particular, the oxidation of the purine bases at carbon electrodes has been exploited for amperometric detection of nucleic acids in flow-injection (Wang, J.; Chen, L.; Chicharro, M. Anal. Chim. Acta, 319, (1996) 347) and capillary-electrophoresis (Xu, D. K.; Hua, L.; Chen, H. Y. Anal. Chim. Acta, 335, (1996) 95) systems. Another electrochemical route under evaluation relies on the oxidation of the sugar backbone at copper surfaces (Singhal, P.; Kuhr, W. G. Anal. Chem., 69, (1997) 4828). Such detection schemes can be used for monitoring both purine- and pyrimidine-containing nucleic acids, but require the use of an alkaline medium and specialized sinusoidal voltammetric instrumentation. In addition to these direct anodic detection schemes, several groups have explored indirect electrochemical protocols for detecting DNA (Takenaka, S.; Uto, Y.; Kondo, H.; Ihara, T.; Takagi, M. Anal. Biochem., 218, (1994) 436; Woolley, A. T.; Lao, K.; Glazer, A.; Mathies, R. A. Anal. Chem., 70, (1998) 684).

One application for biosensing devices is the in situ detection of DNA hybridization. Methods and devices for combining the base-pair recognition of DNA probes with the advantages of electrochemical transducers are currently receiving significant attention due to numerous potential applications (E. K. Wilson, Chem. Eng. News, May 25, 1998, 47; S. R. Mikkelsen, Electroanalysis 8(1996) 15). Most of these devices rely on measuring changes in the peak current of a redox-active marker that preferentially binds to the duplex formed in the hybridization event (K. M. Millan, S. R. Mikkelsen, Anal. Chem. 65(1993) 2317; K. Hashimoto, K. Ito, Y. Ishimori, Anal. Chem. 66(1994) 3830). Label-free electrochemical detection of hybridization reactions represents a very attractive approach for detecting DNA sequences (H. Korri-Youssoufi, F. Garnier, P. Srivastava, P. Godullot, A. Yassar, J. Am. Chem. Soc. 119 (1997) 7388; P. Bauerle, A. Emge, Adv. Mater., 10(1998) 324; J. Wang, G. Rivas, J. Fernandes, L. Paz, M. Jiang, R. Waymire, Anal. Chim. Acta 375(1998) 197; and E. Souteyrand, J. P. Cloarec, J. R. Martin, C. Wilson, I. Lawrence, S. Mikkelsen, M. F. Lawrence, J. Phys. Chem. B 101(1997) 2980). Such approaches rely on monitoring changes in electronic or interfacial properties accompanying the DNA hybridization event. Label-free detection thus greatly simplifies the sensing protocol, since it eliminates the need for indicator addition, association and detection steps, and potentially offers instantaneous detection of the duplex formation.

Conducting-polymer molecular interfaces hold particular promise for inducing electrical signals resulting from DNA interactions. Changes in the properties of conducting polymers accompanying DNA hybridization have been reported in connection with the electropolymerization of oligonucleotide-substituted films (Korri-Youssoufi et al., supra; Bauerle et al., supra; U.S. Pat. No. 5,837,859). However, all such reported methods have been indirect, such as the method of Korri Youssoufi et al., which employs functionalized conjugated polymers, with an amino-substituted oligonucleotide grafted on a precursor copolymer, or the method of U.S. Pat. No. 5,837,859, employing copolymerization utilizing a covalent bond, such as with a spacer arm. Other methods, such as that of U.S. Pat. No. 5,156,810, employ a polymerized surfactant layer incorporating a ligand on a substrate. Other patents of interest include U.S. Pat. No. 5,776,672, which employs secondary substrates and requires approximately one hour per assay. The immobilization of DNA onto conductive surfaces is of enormous interest both in studies of DNA itself and numerous applications ranging from DNA diagnostics to gene therapy. A key requirement for such investigations and applications is the achievement of an efficient interface between the nucleic acid system and the conductive surface.

SUMMARY OF THE INVENTION (DISCLOSURE OF THE INVENTION)

In one embodiment, the invention is an apparatus for detection of DNA hybridization, which apparatus includes a specimen electrode with a detection surface and a conducting polymer composition coating at least a portion of the detection surface of the specimen electrode, wherein the conducting polymer composition comprises a conducting polymer and a free oligomer complementary to the DNA sequence to be detected. The oligomer is free in that the oligomer is not conjugated or bonded to the conducting polymer or any secondary substrate. The specimen electrode may be a carbon, metallic or metal-coated crystal electrode. The conducting polymer may be an electropolymerized substance, such as polypyrrole, polythiophene, polyaniline or a derivative thereof. The free oligomer can be an oligonucleotide from about 8 to about 50 mers, and preferably from about 20 to about 30 mers.

The apparatus for detection of DNA hybridization can include means for accumulating a specimen on at least a portion of the polymer coated detection surface of the specimen electrode and means for amperometric detection of the specimen electrode upon accumulation of a specimen on at least a portion of the polymer coated detection surface of the specimen electrode. Means for accumulating a specimen can include a reservoir or other receptacle or volume, and can also include pumps, shunts, tubes and other structure for accumulating a specimen. Means for amperometric detection can include any metering or measuring device or system for amperometric and other electric current-related measurements, which may be digital or analog, and which may be optionally integrated into a computer-based system.

The apparatus for detection of DNA hybridization can further include a reference electrode and means for determining the change in potential of the specimen electrode relative to the reference electrode upon accumulation of a specimen on at least a portion of the polymer coated detection surface of the specimen electrode.

In another embodiment, the invention provides a method for detection of DNA in a test specimen, including the steps of:

providing a specimen electrode with a detection surface;

coating at least a portion of the detection surface with a conducting polymer composition, which composition includes a conducting polymer and a free oligomer complementary to the DNA sequence to be detected;

providing electrical contact to the specimen electrode;

exposing at least a portion of the conducting polymer composition coated detection surface of the specimen electrode to a solution containing the test specimen; and detecting interactions of the free oligomer and DNA contained in the test specimen.

In the foregoing method, the oligomer is free in that the oligomer is not conjugated or bonded to the conducting polymer or any secondary substrate. The oligomer is complementary to the DNA sequence to be detected if it can be hybridized with the DNA sequence to be detected, even though there may not be a one-for-one correspondence between all base pair members.

In the foregoing method, detecting can be by electrochemical means. One such electrochemical means is determining the change in potential of the specimen electrode relative to a reference electrode upon exposing the specimen electrode to a solution containing the test specimen.

In the method, coating can be by electrochemical deposition of the composition including the conducting polymer and the free oligomer complementary to the DNA sequence to be detected. The electrochemical deposition can be by cyclic voltammetric deposition.

The method can also include the step of electropolymerizing a substance to form the conducting polymer. The substance to be electropolymerized can be a pyrrole, thiophene, aniline or derivative thereof.

In another embodiment, the invention provides an apparatus for detection of nucleic adds in a flowing stream, which apparatus includes a first test electrode with a detection surface, a conducting polymer containing a first dopant coating at least a portion of the detection surface of the first test electrode, means for providing electrical contact to the first test electrode, means for flowing a liquid stream in contact with at least a portion of the detection surface of the first test electrode, and means for detecting nucleic adds in the flowing stream by amperometric detection of adsorption of nucleic adds onto the conducting polymer of the first test electrode. The apparatus can also include a reference electrode in contact with the liquid stream, means for providing electrical contact to the reference electrode, and means for amperometric detection of the first test electrode relative to the reference electrode. The apparatus can further also include a second test electrode with a detection surface, a conducting polymer containing a second dopant coating at least a portion of the detection surface of the second test electrode, means for providing electrical contact to the first test electrode, means for flowing the stream in contact with at least a portion of the detection surface of the second test electrode and means for detecting nucleic acids in the flowing stream by amperometric detection of absorption of nucleic acids onto the conducting polymer of the second test electrode.

In the apparatus for detection of nucleic acids in a flowing stream the conducting polymer can include an electropolymerized substance. The electropolymerized substance can be polypyrrole, polythiophene, polyaniline or a derivative of any of the foregoing. The first and second test electrodes can be carbon, metallic or metal-coated crystal electrodes, and it is possible and contemplated that the first and second test electrodes may differ. Similarly, where a first and second test electrode are employed, the first dopant and second dopant may differ.

In yet another embodiment the invention provides a method for nucleic add detection in a flowing stream, including the steps of:

coating a first test electrode with a conducting polymer containing a first dopant;

providing electrical contact to the first test electrode;

exposing the first test electrode to a flowing steam; and detecting nucleic acids in the flowing stream by amperometric detection of adsorption of nucleic acids onto the conducting polymer.

The method for nucleic acid detection in a flowing stream can also optionally include the following additional steps:

providing a reference electrode;

providing electrical contact to the reference electrode; and measuring current changes in the first test electrode relative to the reference electrode.

The method for nucleic acid detection in a flowing stream can further optionally include the following additional steps:

coating a second test electrode with a conducting polymer containing a second dopant;

providing electrical contact to the second test electrode;

exposing the second test electrode to the flowing stream sequentially with exposing the first test electrode and reference electrode to the flowing steam; and characterizing nucleic acids in the flowing stream by differences in amperometric detection of adsorption of nucleic acids onto the conducting polymer of the second test electrode and the first test electrode.

In this method for nucleic acid detection in a flowing stream both the first and second dopant can be anionic, and either can be a source of nitrate ion or an oligonucleotide. Different dopants can be utilized to yield different detection signals using the same specimen, so that the specimen may be characterized by differences in the detection signals between the first and second test electrodes.

The step of coating the test electrodes includes coating by electrochemical deposition of the conducting polymer and the dopant. The electrochemical deposition can be by cyclic voltammetric deposition. This method can also include the step of electropolymerizing a substance to form the conducting polymer. The substanced to be electropolymerized can be pyrrole, thiophene, aniline or derivative thereof.

A primary object of the present invention is to provide methods and compositions for the rapid, label-free electrochemical detection of nucleic acids, including oligonucleotides, DNA and RNA.

Another object of the present invention is to provide methods and compositions for label-free electrochemical detection of DNA hybridization.

Another object of the present invention is to provide methods and compositions for electrochemical detection of DNA hybridization utilizing an electropolymerized film wherein the sole dopant is the oligonucleotide probe.

Another object of the invention is to provide methods and compositions for electrochemical detection of DNA hybridization wherein distinct hybridization peak signals are observed in the presence of both complementary and non-complementary DNA sequences, with the peaks being of opposite direction for complementary and non-complementary DNA sequences.

Another object of the invention is to provide methods and compositions for electrochemical detection of nucleic acids utilizing conducting polymer electrodes using flow injection analysis.

Another object of the invention is to provide methods and compositions utilizing polymeric films, such as polypyrrole, polythiophene or polyaniline, for flow injection analysis, such as in chromatography or electrophoresis systems, wherein detection of nucleic acids results from rapid adsorption and desorption of nucleic acids onto the film during the passage of the sample over a film-coated electrode.

A primary advantage of the present invention is that, in one embodiment, it provides a fast, sensitive, label-free and universal method for the detection of oligonucleotides, DNA and RNA.

Another advantage of the present invention is that, in one embodiment, it provides methods and compositions for detection of nucleic acids utilizing a polymeric film, such as polypyrrole, polythiophene or polyaniline, wherein a nucleic acid is the sole dopant within the polymeric film, and serves as the sole charge compensating counter ion during film formation.

Another advantage of the present invention is that it provides methods and compositions for detection of nucleic acids and hybridization events utilizing a polymeric film, such as polypyrrole, polythiophene or polyaniline, wherein the detection scheme can discriminate against oxidizable non-nucleic acid species present in biological samples.

Another advantage of the present invention is that it provides methods and compositions which may be employed as biomaterials for genoelectronic devices, composite materials, bioactive interfaces, flow systems, microscale separations, "on-chip" devices and similar biomaterial-based devices, for use in genetic analysis, diagnostic applications, microscale separations, on-line PCR amplification, batch injection analysis, hybridization analysis and the like.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 1a is a depiction of an electropolymerization cell and FIG. 1b is an enlarged view of the portion of the elecropolymerization including glassy carbon substrate electrode 1, drop 2 of pyrrole monomer solution containing the oligonucleotide, and Ag/AgCl reference electrode 3;

FIG. 2 depicts repetitive cyclic voltammograms for polypyrrole ("PPy") polymerization reactions on a glassy carbon electrode;

Figure 3:
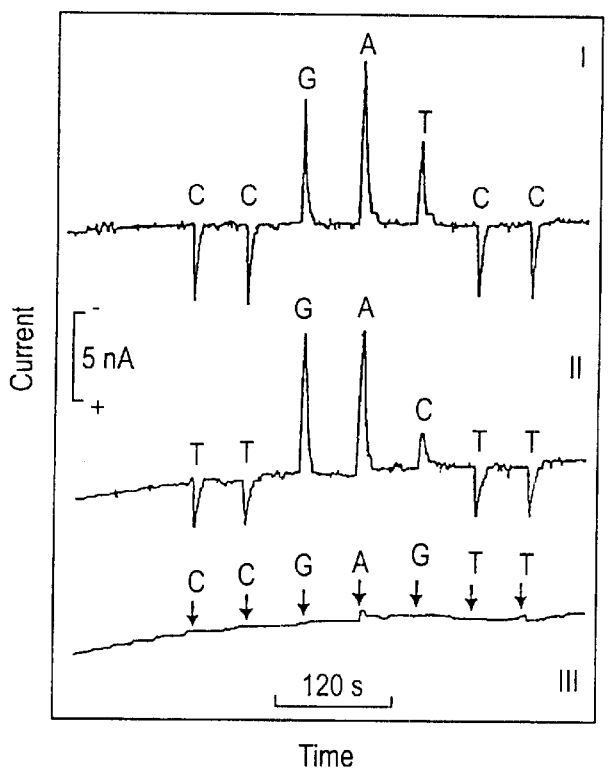
FIG. 3 depicts current-time hybridization signals recorded in situ using modified electrodes with addition of different complementary and non-complementary oligonucleotides strands.

DESCRIPTION OF THE PREFERRED EMBODIMENTS BEST MODES FOR CARRYING OUT THE INVENTION

Nucleic Acid Doped Probes within Conducting Polymer Films

Using the methods and devices of this invention, conducting polymer-coated electrodes may be doped with nucleic acids, and used for detection of nucleic acids. The nucleic acid may be the sole dopant added to the conducting film, and may be added during electropolymerization of the film. The nucleic acid serves as the sole counter anion or dopant during the growth of the conducting film, and further maintains its ability to bind complementary nucleic acids while within the polymeric film. The nucleic acid doped probes within the conducting polymer film may be utilized to detect hybridization events when exposed to a sample containing a nucleic acid complementary to nucleic acid within the film, and may further be used to detect samples containing non-complementary nucleic acids.

Any art conventional electrodes may be employed, and particularly glassy carbon electrodes, carbon paste electrodes, metallic electrodes, metal-coated crystal wafer electrodes, and other electrodes. A counter electrode may optionally be employed, such as a platinum electrode, and a reference electrode, such as an Ag/AgCl electrode. In such methods, the glassy carbon, carbon paste or similar test electrode is coated with a polymeric film, such as by cyclic voltammetric electrodeposition of the film from an aqueous solution containing the monomer and dopant. In one embodiment, a polypyrrole film is prepared by multiple cycle voltammetric deposition onto a glassy carbon electrode immersed in a 0.05 M pyrrole solution containing 100 $\mu$g/mL of a specified oligonucleotide probe. Any range of cycles and voltages resulting in deposition of a polymeric film may be employed. In one embodiment, 20 cycles between 0.0 and +1.0 V are employed, at a rate of 50 mV/s. Alternatively, the polymeric film containing a nucleic acid dopant or probe is deposited on a gold-coated crystal wafer or other conductive electrode.

Any conducting film that may be electropolymerized may be employed for this invention. The conducting film may be an electropolymerized polypyrrole film, made from pyrrole. Alternatively, other polymerizable coatings may be employed, including but not limited to polythiophene or polyaniline. Derivatives of any of pyrrole, polythiophene or polyaniline may also be employed, as may other polymerizable conducting substrates or materials.

Any of a variety of nucleic acids may be employed as a dopant in the methods of this invention. It is preferable that high purity and desalted nucleic acids be employed, to minimize any dopant effect from impurities or salts. It is hypothesized that larger nucleic acids, on the order of 20 mers or greater, utilized as a dopant irreversibly enter the polypyrrole network. As a result, the electrochemistry is hypothesized to be dominated by the movement of the electrolyte cation by the following formula:

where "PPy" is polypyrrole and "ODN" is the oligonucleotide. Thus a cation-controlled transport mechanism is present, with a frequency rise during oxidation and decrease upon reduction. Such insertion and ejection of the sodium cation may create a "psuedo-dopant" effect.

Various parameters, such as the oligonucleotide length or concentration, and the potential range, have an effect on the properties of the nucleic acid-doped electrode. In one embodiment, low concentrations of the nucleic acid dopant may be employed, on the order of ~1×10$^{-5}$ M, in the absence of additional electrolyte.

Any of a wide variety of nucleic acids may be employed in this invention, including oligonucleotides, DNA, ssDNA and RNA. In one embodiment, oligonucleotides of from about 8 to about 50 mer length, and preferably about 20 to about 30 mer length, and complementary to a DNA sequence to be detected, are utilized. The oligonucleotide need not be fully complementary, in that it need not contain a one-for-one base pair match for the DNA sequence to be detected, so long as the oligonucleotide may be functionally complexed, such that a hybridization event may be detected. The anionic oligonucleotide probes serve as the sole charge-compensating counter ion during the growth of polypyrrole films, retain their hybridization activity upon entrapment within the polypyrrole film, and provide distinct transient hybridization current peaks of opposite directions in the presence of complementary and noncomplementary DNA sequences. The electrode to be used, such as a glassy carbon electrode or metallic electrode, is appropriately cleaned. For glassy carbon electrodes, such cleaning may consist of polishing with fine alumina slurry, such as 0.05 $\mu$m alumina slurry, and washing with sterile and deionised water.

A polypyrrole film is applied by voltammetric deposition on the electrode by immersing the glassy carbon electrode in 0.05 M distilled pyrrole solution containing approximately 100 $\mu$g/mL of the oligonucleotide probe. Prior to immersion of the electrode, polypyrrole electropolymerization is effected, such as by continuous cyclic voltammetric scanning between 0.0 and +0.70 V at a rate of 50 mV/s, using the pyrrole and oligonucleotide solution. The polypyrrole film is prepared by voltammetric deposition, such as 20 cycles between 0.0 and +1.0V at a rate of 50 mV/s, while immersing the glassy carbon electrode in the pyrrole and oligonucleotide solution. Following electropolymerization and deposition, the film-coated surface of the electrode is cleaned, as by rinsing with sterilized water.

Any art convention means of detection utilizing an electrode may be employed. In one embodiment, a two-electrode microcell system is employed, utilizing the polypyrrole- and oligonucleotide-containing film-coated electrode and a reference electrode, such as an Ag/AgCl electrode. Hybridization measurements may be obtained in a two-electrode cell, such as a cylindrical glass cell, containing an appropriate media solution, such as 0.5 ml of a stirred 0.1 M glycine and 0.1 M sodium chloride solution.

An appropriate working potential, such as +0.15 V against the Ag/AgCl reference electrode, is applied and the transient background current allowed to decay. A suitable quantity of the solution containing the specimen to be tested, such as a 25 $\mu$L droplet, is placed over the polypyrrole- and oligonucleotide-containing film-coated electrode. All potentials are reported against the Ag/AgCl reference electrode.

When the solution containing the specimen to be tested contains an oligomer complementary to the oligonucleotide in the polypyrrole film, a defined transient anodic peak is detected. When the solution containing the specimen to be tested contains an oligomer that is non-complementary to the oligonucleotide in the polypyrrole film, a defined transient cathodic peak is detected. Thus in standard detection systems, an opposite direction signal, in relation to baseline, is obtained depending on whether the specimen to be tested contains a complementary or non-complementary oligomer. This thus permits the acquisition of one of three different responses for each sample: no oligomer (no peak), hybridization event (anodic peak), or non-complementary oligomer (cathodic peak).

Conducting Polymer Coated Electrodes for Flow Detection

Conducting polymer-coated electrodes may be used for sensitive, universal, low-potential amperometric detection of oligonucleotides, DNA, and RNA in flowing streams. This method and the associated devices employ a conducting polymeric-coated glassy carbon or other acceptable detector, with detection of nucleic acids by adsorption of oligonucleotides, DNA, and RNA onto the film, rather than detection of electron transfer reactions. The adsorption behavior is facilitated by electrostatic interactions between the negatively charged nucleic acids and the positive charge density of the conducting polymer backbone. The analytical utility of this system may be demonstrated using flow injection analysis (FIA). A modified FIA amperometric protocol leads to well-defined current peaks, reflecting the adsorption and desorption during the arrival and departure of the sample plug from the working electrode compartment. This nucleic acid detection scheme may be used for FIA measurements, and may also be applied to micro-separation and various "on-chip" applications.

In one embodiment for this invention, pyrrole is used as the substrate that is electropolymerized and deposited on the electrode. In addition to pyrrole, other substrates which may be electropolymerized may be employed. These include, but are not limited to, thiophene and aniline and derivatives of any of the foregoing. In general, the substrate to be polymerized must be conducting at essentially neutral pH levels. Any substrate or substance known in the art which may be electropolymerized may be employed in this invention.

The polymeric film is doped with a suitable dopant agent. A source of nitrate ion may be employed as the dopant, such as a solution containing 0.05 M pyrrole and 1.0 M potassium nitrate. However, other dopants may be utilized and are included within the scope of this invention. Such dopants include nitrate, perchlorate and chloride dopants, and other dopants such as phosphate, sodium lauryl sulfate and p-toluenesulfonate. In general, any inorganic or organic anionic substrate may be employed as a dopant.

It is also contemplated that a nucleic acid may be employed as the dopant for use in flow analysis. Any suitable anionic oligonucleotide may serve as the sole charge compensation counter ion during electrochemical deposition of the polymeric substrate.

It is to be understood and is contemplated that the choice of dopant may significantly alter the specificity and selectivity of the detection system to certain or specific nucleic acids, and may thereby permit selection and discrimination between various nucleic acids, such as different base sequence oligonucleotides, DNA and RNA, different length oligomers, and the like. It is also understood and contemplated that two or more electrodes, each utilizing a different dopant, polymeric substrate or combination thereof, may be serially employed in a detection scheme, such that two or more electrodes may be used to detect the same sample, and thereby provide specific discrimination. It is further to be understood and contemplated that a single electrode surface may include two or more distinct and different areas or sections coated with a film utilizing a different dopant, polymeric substrate or combination thereof such that multiple signals and more than one information set may be obtained from a single electrode.

Any suitable electrode may be utilized, including any electrode known in the art. Such electrode may be carbon or metal based, and may include crystal elements. Representative electrodes that may be employed include glassy carbon electrodes, carbon paste electrodes, platinum electrodes, gold electrodes, copper electrodes, metal-coated crystal electrodes, and the like. Such electrodes may be specifically designed or constructed for use in flow detection systems.

The electrode, however made, may be coated with the doped substrate by any means known in the art. In one embodiment, a 500 $\mu$L solution containing 0.05 M pyrrole and 1.0 M potassium nitrate is prepared, and the electrode is immersed in the solution. The film is deposited by cyclic voltammetric electrodeposition, such as by scanning the potential between 0.0 and 0.7 V, against a reference electrode such as an Ag/AgCl electrode, at a rate of 50 mV/second for ten cycles. It is to be understood and is contemplated that the electrodeposition parameters may be significantly and substantially altered, and that any means by which electrodeposition can be achieved may be employed. Thus, the potential difference may be changed, the cycle rate may be changed, and the number of cycles employed may be changed. The film may also be electrodeposited under either fixed potential or fixed current conditions.

Any suitable voltammetric detection system may be employed. In a conventional system, a working electrode is employed, such as a glassy carbon electrode, which is coated with the doped polymeric film, such as polypyrrole doped with nitrate ion, by electrodeposition means. A specific counter electrode may be employed, such as a platinum counter electrode, and a reference electrode is conventionally employed, such as an Ag/AgCl reference electrode. However, any method or means by which potential differences may be detected or determined may be employed in using the method of this invention.

A flow or batch cell of some nature is employed, which contains the coated working electrode and optionally the counter and reference electrode. Conventionally, potential differences are reported with respect to the reference electrode, but any potential difference referent means or method may be employed, provided it yields a signal as hereafter described.

Any art conventional flow system may be employed. In one embodiment, the flow injection system includes a carrier fluid reservoir, an injection valve and port assembly with a 20 $\mu$L sample loop, and a suitable pump, such as a peristaltic pump. In an alternative embodiment, the flow or batch cell is placed in series in a chromatography or electrophoresis system, for detection of nucleic acids following chromatographic or electrophoretic separation.

The carrier fluid reservoir may include any suitable carrier solution, such as a 0.1 M sodium chloride solution. Any appropriate flow rate may be employed, which may empirically be determined based on the detection rate and limits of the system. In one embodiment, a flow rate of 0.6 mL/minute is employed. The flow rate may have a significant effect on the measured change in potential. Thus, in some systems the potential response may change rapidly and linearly upon increasing the flow rate from 0 to a higher flow rate, such as about 0.48 mL/minute, and may thereafter level off at higher flow rates.

Prior to sample detection, the working potential may be applied while flowing the carrier solution, and the transient background current allowed to decay to a stable value. In one embodiment, the working potential is −0.15 V relative to the reference electrode. It is possible and contemplated that decay to a stable value may be facilitated by step-wise decrease of the applied potential to the working potential, such as −0.15 V. In one embodiment, two such preceding potential steps are utilized, for approximately 50 seconds per step. Other working potentials may be employed, and may be determined empirically. In general, a working potential is selected that provides the optimal signal with the minimum background noise. In general, background noise is observed at more negative potentials, and in at least some systems, the signal response starts at potentials lower than about +0.40 V. A potential independent signal response may be obtained at lower potentials. The −0.15 V working potential provided, in one embodiment, an optimal signal with minimal background noise.

Once the measured potential difference has stabilized, test samples may be injected into the system, such as by use of the injection value and port assembly. The analyte is detected by means of potential difference. In general, the working potential rapidly increases in current upon detection, with fast return to baseline. Response times to reach 90% of the maximum signal are about three seconds or less, depending in part upon flow rate. Peak width is similarly determined, in part, by the flow rate.

The concentration of analyte in the test sample determines, in part, the height of the amperometric peak observed. The amperometric peak, measuring the potential difference due to the analyte, is concentration dependent. Thus, a 20-mer oligonucleotide may be detected at concentrations over a range from about 1 to over 10 $\mu$g/mL, which corresponds to about 20 to 200 pg for a 20 mL injection. It is possible and contemplated that lower sample concentrations may be detected, including samples at picogram levels.

Industrial Applicability of Nucleic Acid Doped Probes within Conducting Polymer Films The hybridization recognition devices and methods of this invention permit very simple sensing protocols, with no need for discrete indicator addition, association or detection steps, and further permit functionally instantaneous detection of duplex formation. Use of nucleic acid doped probes within conducting polymer films for detecting DNA sequences may be used for a wide range of diagnostic applications. Confinement of DNA probes within the electrode film offers major advantages, including simplification of the sensing protocol by obviating the need for time-consuming derivatization reactions, providing improved conductivity and mechanical properties compared to the use of covalently-anchored monomers, providing unique, in-situ and instantaneous hybridization signals compared to the ex-situ detection and approximately 2 hour hybridization employed with functionalized monomers, and permitting localization of probes onto miniaturized surfaces, such as are desired for DNA diagnostic devices.

Well-defined hybridization peaks at a concentration of approximately 1 mg/L of the suspected oligomer to be tested can be obtained with very short hybridization periods, on the order of a few seconds. The peak width, approximately 15 seconds in duration, and rapid return to the baseline permits repeat measurements at a rate of at least 60 samples per hour with a single test electrode. This is substantially faster than the prolonged hybridization period, of approximately two hours, required with polymers incorporating covalently anchored probes.

The mechanism by which opposite direction peaks are obtained for complementary and non-complementary oligomers has not been fully elucidated. The response may reflect changes in the conductivity of the polypyrrole network. No signals were observed in control experiments involving probes entrapped in a nonconducting polyphenol network. The decreased current upon adding the complementary target may reflect increased charged density and size of the nucleic acid dopant during hybridization, based on temporary double-strand anions as opposed to single-strand anions, with concomitant changes in polypyrrole conductivity. The opposite or cathodic response to the non-complementary oligomer strands may be attributed to conductivity or capacitance changes associated with their electrostatic repulsion or adsorption. Similarly, the mechanism for the transient nature of the response has not been fully elucidated. Transient signals are attained in a stirred batch solution, in response to the sample injection before it is dispersed over the entire cell volume. The transient signals may reflect short-term disturbances of the $\pi$ conjugation of the polypyrrole backbone, such as reversible changes in the film conductivity. It is also possible that changes in film capacitance, leading to a current flow until charge compensation is re-established, are related to the transient nature of the observed peaks.

Altering the working potential against the Ag/AgCl or other reference electrode alters the signal obtained. Thus, a more negative working potential, such as −0.15V against an Ag/AgCl reference electrode, yields a stepwise, steady-state hybridization signal. However, the peak-shaped response, with a rapid return to the baseline, observed at more positive working potentials, such as +0.15V, yields additional information for certain diagnostic applications.

The hybridization recognition devices and methods of this invention may be utilized for a wide variety of DNA diagnostics. Applications include, without limitation, diagnosis of genetic or infectious diseases, environmental testing for bacterial or other organic contamination, rapid detection of certain warfare agents, forensic investigations and the like. For many applications of this invention, DNA biosensors, which are small analytical devices including a nucleic-acid recognition layer of this invention immobilized on a physical transducer, and preferably an electrochemical transducer, may be employed. In such DNA biosensors, the DNA hybridization event produces a useful analytical signal. Electrochemical transducers have high sensitivity, minimal power requirements and are compatible with microfabrication and miniaturization technologies.

In one embodiment, the hybridization recognition devices and methods of this invention may be employed on transistor-like electronic devices based on the electrodeposition of nucleic acid-containing conducting polymers across the gap between closely-spaced microband electrodes. In such embodiments, utilizing microfabrication and micromachining technologies, high-density arrays of individually addressable nucleic acid-doped polymer film coated microelectrodes may be employed. A microfluidic network may be used to integrate sample transport, reactions, DNA amplification, separation or detection, all on essentially a "chip" format. In such a system, the electrochemical control can be integrated on the chip.

Industrial Applicability of Conducting Polymer Coated Electrodes for Flow Detection The conducting polymer-coated electrodes and methods of this invention may be employed for flow detection in a wide variety of industrial, biotechnological and diagnostic applications. Oligonucleotides, DNA and RNA may be detected, and may be discriminated against easily oxidizable species. Different response patterns observed in the presence of different dopants may be utilized to develop multi-electrode nucleic-acid arrays, such that differential determinations may be made utilizing serial or parallel multi-electrode nucleic acid detection arrays.

The conducting polymer-coated electrodes and methods of this invention may be employed for flow detection in a variety of flow systems, including but not limited to microscale separation systems, such as chromatography or electrophoresis separation systems, other separation systems, PCR amplification systems, and the like. Very small-scale systems may be employed, including systems utilizing microfabrication and micromachining technologies, wherein high-density arrays of individually addressable doped polymer film-coated microelectrodes may be employed. These embodiments include the on-chip formats discussed above. These high-density arrays may exploit the different response patterns and cross-reactivity at films prepared with different dopants or pyrrole derivatives, resulting in an integrated system that can differentially determine constituent nucleic acid elements in a flowing stream.

It is also possible and contemplated that the conducting polymer-coated electrodes and methods of this invention for flow detection may be employed with and combined with the hybridization recognition devices and methods of this invention, such that one or more of either serial or parallel electrode detectors, which may include biosensors employing electrochemical transducers, can be employed, permitting detection of hybridization events as well other conducting polymer determinations.

The invention is further illustrated by the following non-limiting examples.

EXAMPLE 1

Experiments were performed at room temperature, using a CHI 620 Electrochemical Analyzer (CH Instruments, Cordova, Tenn.) connected to an IBM 586 computer. A two electrode microcell, comprising a glassy-carbon working electrode (3 mm diameter, BAS) and an Ag/AgCl (3M NaCl) reference, was employed during the electropolymerization. The electrode is depicted in FIG. 1. In FIG. 1, the components include (1) glassy carbon substrate electrode; (2) drop of pyrrole monomer solution containing the oligonucleotide; (3) Ag/AgCl electrode; (4) Teflon sleeve; (5) rubber stopper; and (6) contact. The glassy carbon substrate electrode was placed in an inverted position opposite to the reference electrode. A 25 $\mu$l droplet of the preparation solution was placed over the glassy carbon substrate electrode disk. All hybridization measurements proceeded in a two-electrode cylindrical glass cell, containing 0.5 ml of a stirred glycine/sodium-chloride solution, with both electrodes faced downwards.

The various oligonucleotides were purchased as desalted products from Life Technologies (Grand Island, N.Y., USA). Pyrrole (Aldrich) was distilled and kept refrigerated under nitrogen prior to use. The molecular weights of the oligonucleotide used were 6,845 (oligo(dG)$_{20}$), 6,525 (oligo (dA)$_{20}$), 6,045 (oligo(dC)$_{20}$), and 6,345 (oligo(dT)$_{20}$). The glycine-NaCl solution (0.1 M) was used as the medium for hybridization and control experiments.

The glassy carbon electrode was polished with a 0.05 $\mu$m alumina slurry and thoroughly washed with sterilized water. The polypyrrole electropolymerization proceeded by a continuous cyclic voltammetric scanning (between 0.0 and +0.70V; 50 mV/s) using a 0.05 M pyrrole and 100 $\mu$g/mL oligonucleotide probe solution. The polypyrrole film was prepared by voltammetric deposition (20 cycles between 0.0 and +1.0V; 50 mV/s), while immersing the glassy carbon electrode in the 0.05M pyrrole 100 $\mu$g/mL oligonucleotide probe solution. Following electropolymerization, the modified surface was rinsed with sterilized water. Hybridization measurements were conducted using a stirred 0.5 ml 0.1M glycine/0.1M NaCl blank solution containing the working and reference electrodes. The working potential (+0.15V vs. Ag/AgCl(3M NaCl)) was applied and the transient background current was allowed to decay before adding test complementary and noncomplementary oligomers. All potentials were reported against the Ag/AgCl reference electrode.

EXAMPLE 2

Using the method of Example 1, nucleic acid entrapped probes were constructed and utilized without an added electrolyte, with the anionic oligonucleotide serving as the sole dopant. This produced high quality, strongly adhered purple films. FIG. 2 displays repetitive cyclic voltammograms recorded during the electropolymerization of PPy onto the glassy-carbon substrate in the presence of $1.6 \times 10^{-5}$M of the 20-mer oligo(dG)$_{20}$ probe (A), and 1.0M potassium chloride (B). The probe solution included 0.05 M pyrrole and 100 $\mu$g/mL oligo(dG)$_{20}$ for (A), and 0.05 M pyrrole and 1.0 M KCl for (B). Continuous cyclic sweeping at 50 mV/s was utilized. The use of the oligonucleotide and electrolyte solutions revealed normal polymer growth with increasing current upon repetitive scanning over most of the potential range. The large current response observed in the electrolyte-free oligo(dG)$_{20}$ solution upon repetitive cycling was indicative of efficient film deposition. A slower growth profile, nearly completed within the first 10 cycles, was observed in the potassium chloride solution probes. The PPy/oligo(dG)$_{20}$ film displayed a wider conductive region, especially in the cathodic region, and up to at least $-0.8V$. A similar trend, with a slightly slower growth of the PPy film, was observed with incorporation of an oligo(dA)$_{20}$ into a PPy film. The nucleic-acid probes did not undergo any redox activity over the potential window shown in FIG. 2. While micromolar levels of the oligonucleotide were sufficient for film preparation, significantly higher chloride concentrations ($>5 \times 10^{-2}$ M) were require to produce good quality conducting films using potassium chloride. No electropolymerization was obtained using a $1 \times 10^{-3}$ M potassium chloride solution.

EXAMPLE 3

In this series, the method of Example 1 was utilized for label-free, in situ detection of complementary DNA strands. FIG. 3 displays the current-time response of PPy/oligo (dG)$_{20}$ (I), PPy/oligo(dA)$_{20}$ (II), and PPy/Cl$^-$ (III) modified electrodes to addition of different complementary and non-complementary oligomers. The oligomers added included (I) four 10 $\mu$g/ml additions of oligo(dC)$_{20}$ (C), and 20 $\mu$g/mL additions of oligo(dG)$_{20}$ (G), oligo(dA)$_{20}$ (A), and oligo (dT)$_{20}$ (T); (II) four 10 $\mu$g/ml additions of oligo(dT)$_{20}$ and 20 $\mu$g/ml additions of oligo(dG)$_{20}$, oligo(dA)$_{20}$, and oligo (dC)$_{20}$; and (III) several 20 $\mu$g/ml additions of oligo(dC)$_{20}$, oligo(dG)$_{20}$, oligo(dA)$_{20}$, and oligo(dT)$_{20}$. The hybridization medium employed was 0.1 M glycine and 0.1 M NaCl, with an applied potential of +0.15 V against the reference Ag/AgCl electrode in 3M NaCl. Films I and II were prepared using 13 and 26 potential cycles, respectively.

Both PPy/probe-modified electrodes displayed defined transient anodic peaks upon adding the complementary targets, and opposite or cathodic signals upon spiking with non-complementary oligonucleotides. The direction of these signals relative to the baseline was clearly dependent upon the sequence of the probe dopant and of the added or test oligomers. This thus permitted both a specific positive or downward signal for complementary oligonucleotides, and a specific negative or upward signal for non-complementary oligomers. Negligible response was observed at the PPy/Cl⁻ coated surface, as shown in (III) in FIG. 3. Well-defined hybridization peaks were obtained at 1 mg/L target concentrations, with very short hybridization periods, on the order of a few seconds. The peak width of approximately 15 seconds and the rapid return to the baseline permitted repetitive target measurements at a rate of 60 samples per hour. Similar experiments at a more negative potential of −0.1 5V yielded a stepwise, steady-state hybridization signal.

EXAMPLE 4

Figure 4:
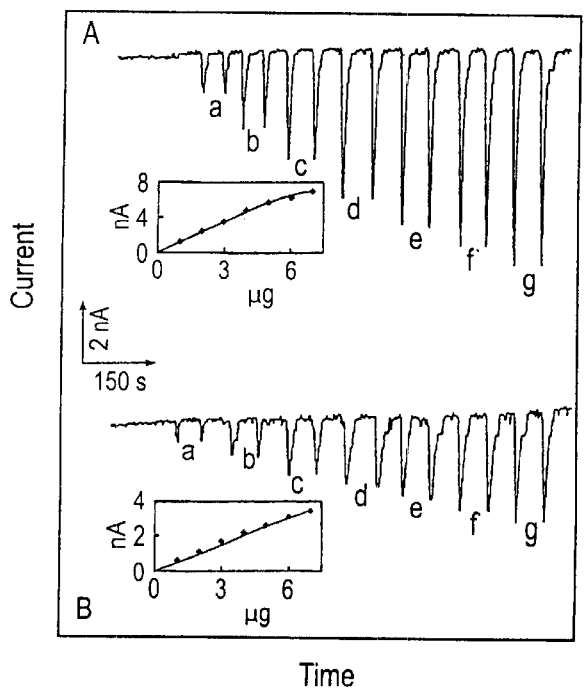
FIG. 4 depicts current-time hybridization signals recorded in situ using modified electrodes with different $\mu$g incremental increases in the level of target and the resulting calibration plots.
Figure 5:
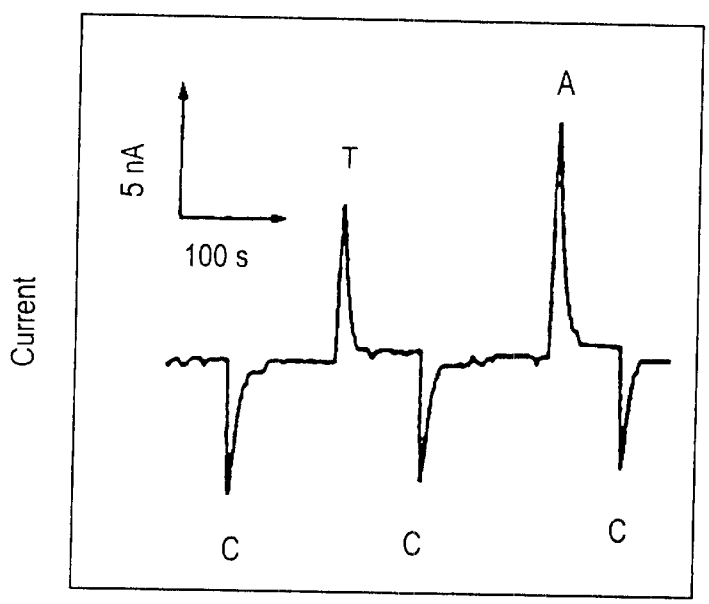
FIG. 5 depicts amperometric response with addition of various oligomers.

In this example, the method of Example 1 was utilized to demonstrate the linearity and reproducibility of the response. FIG. 4 displays the response of the PPy/oligo(dG)$_{20}$ (A) and PPy/oligo(dA)$_{20}$ (B) electrodes to increasing levels of the complementary oligo(dC)$_{20}$ and oligo(dT)$_{20}$ oligomers, respectively. As shown in FIG. 4, the levels of complementary oligonucleotides was increased step-wise from 1 µg (a), to 2 µg (b), 3 µg (c), 4 µg (d), 5 µg (e), 6 µg (f), and 7 µg (g) for each of the oligo(dC)$_{20}$ and oligo(dT)$_{20}$ targets. Also included in FIG. 4 are the resulting calibration plots. While the PPy/oligo(dA)$_{20}$-modified electrode responded linearly to the quantity of the added target, with a sensitivity of 0.52 nA/µg, the response of the PPy/oligo (dG)$_{20}$-modified electrode started to level off above 6 µg, a sensitivity in the linear portion of 1.08 nA/µg. A series of 8 repetitive additions of 6 µg/ml of oligo(dC)$_{20}$ to the PPy/oligo(dG)$_{20}$-modified electrode yielded a reproducible current response with a relative standard deviation of 7.3% and a mean peak current of 4.2 nA. The reproducibility of the target signals was not affected by intermittent additions of excess non-complementary oligomers. FIG. 5 displays the amperometric response of the PPy/oligo(dG)$_{20}$-modified electrode to alternate additions of 10 µg/ml of the oligo(dC)$_{20}$ target and 50 µg/ml of non-complementary oligo(dT)$_{20}$ and oligo(dA)$_{20}$ oligomers. The oligo(dC)$_{20}$ signals were not influenced by the 5-fold excess of the noncomplementary oligomers.

EXAMPLE 5

Voltammetric and flow-injection experiments were carried out with a CHI-620 Electrochemical Analyzer (CH Instruments, Cordova, Tenn.) with an IBM 586 computer. Cyclic voltammetry was performed in a batch cell containing the working electrode disk (bare glassy carbon, modified glassy carbon or carbon paste electrode; 3 mm diameter, BAS), the platinum counter-electrode and an Ag/AgCl (3 M NaCl) reference electrode (BAS). The electrodes were connected to the cell through holes in the Teflon cell cover. All reported potentials were measured with respect to the Ag/AgCl reference electrode. The flow-injection system consisted of a carrier reservoir, a Rainin Model 501 injection valve with 20 µL sample loop, interconnecting Teflon tubing, a VWR peristaltic mini-pump and a homemade large-volume wall-jet detector. The solution inlet was kept 1 mm away from the center of the working electrode. Prior to use, the glassy carbon electrode was polished sequentially with 1.0 µm and 0.05 µm alumina powders on polishing pads and was thoroughly rinsed with water.

PPy film was prepared at the beginning of each day. The PPy-coated glassy-carbon electrode was prepared by cyclic voltammetric electrodeposition of the film from an aqueous solution containing the pyrrole monomer and different dopants (usually nitrate ion). Most applications involved films that were deposited upon scanning the potential between 0.0–0.7 V, against the Ag/AgCl electrode, at a rate of 50 mV/s for ten cycles using a 500 µL preparation solution containing 0.05 M pyrrole and 1.0 M potassium nitrate. The carbon-paste electrode was prepared in a similar fashion.

Transfer RNA (tRNA from Bakers yeast), double-stranded calf thymus DNA and single stranded calf thymus DNA were utilized. The 20-mer oligo (deoxyadenylic acid) (oligo(dA)$_{20}$), 20-mer oligo (deoxycytidylic acid) (oligo (dC)$_{20}$), 20-mer oligo (deoxyguanylic acid) (oligo(dG)$_{20}$), 20-mer oligo (deoxythymidylic acid) (oligo(dT)$_{20}$) and other oligonucleotides with random sequences were purchased from Life Technologies (Grand Island, N.Y.). Pyrrole and aniline were distilled and stored in 10° C. under nitrogen. Sodium lauryl sulfate and sodium p-toluenesulfonate were used as received. L-ascorbic acid and acetaminophen were used as freshly made solutions. A 0.1 M NaCl solution served as the carrier and electrolyte solution during all flowing injection operations.

Flow injection experiments were conducted using the 0.1 M NaCl solution flowing at 0.6 mL/min. Detection was performed after applying the working potential (−0.15 V) while the carrier solution was flowing, and allowing the transient background current to decay to a stable value. Two shorter preceding potential steps, of approximately 50 seconds, to −0.15 V facilitated the background stabilization. The data were collected after smoothing and filtering (using 49 least square points). The PPy film was removed at the end of each series of experiments by a vigorous polishing using 1.0 and 0.05 µm alumina slurries. All experiments were performed under ambient conditions.

EXAMPLE 6

Figure 6:
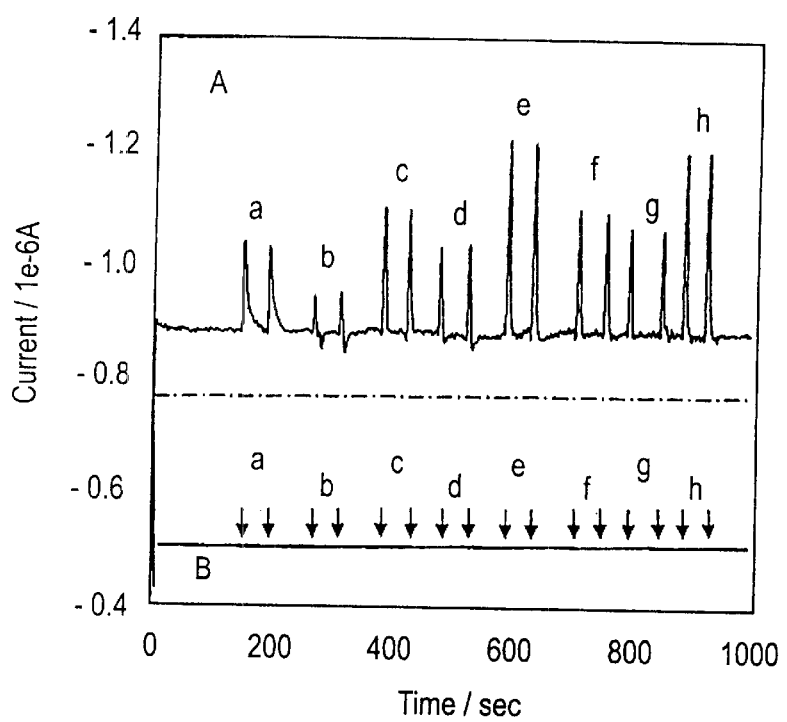
FIG. 6 depicts flow-injection amperometric peaks at the PPy/$NO_3^-$-coated (A) and bare (B) glassy-carbon detectors towards different nucleic acids.

Using the method of Example 5, a total of eight different oligonucleotides and chromosomal DNA and RNA were compared for flow-injection response using PPY-coated glassy carbon detectors and bare glassy carbon detectors. The results are shown in FIG. 6, with the flow injection amperometric peaks at the PPy/NO$_3$⁻-coated (A) and bare (B) glassy-carbon detectors shown towards different nucleic acids: oligo(dT)$_{20}$ (a); tRNA (b); oligo(dA)$_{20}$ (c); ssDNA (d); dsDNA (e); 25-mer oligonucleotide with sequence 5'-TGCCGCTCATCCGCCACATATCCTG-3' (SEQ ID NO: 1), specific to the *Escherichia coli* genome (f); oligo(dG)$_{20}$ (g); and oligo(dC)$_{20}$ (h). The concentration of each nucleic acid was 10 µg/mL, with a flow rate of 0.6 mL/minute, a carrier of 0.1 M sodium chloride, applied potential of −0.15 V and a sample volume of 20 µL.

The bare glassy-carbon electrode showed no response to injection of any of the nucleic acids. All nucleic adds were readily detected at the PPy/NO$_3$⁻-coated glassy-carbon electrode. The detector system exhibited a rapid increase in the current with a fast return to the baseline, characteristic of flow-injection experiments. Response times to reach 90% of the maximum signal were approximately 3 seconds, and the peak widths, at 0.6 C$_{max}$, were approximately 7 seconds. The data demonstrate that the method works with different types of nucleic acids, and that detector sensitivity is not dependent upon the size or composition of the analytes. In similar experiments, the order of the injected oligonucleotides was changed with no apparent changes in sensitivity observed.

EXAMPLE 7

Using the method of Example 5 and the test nucleic acids of Example 6, the effect of different counter ions incorporated into the PPy film was evaluated. The use of nitrate, perchlorate, and chloride dopants yielded well-defined responses to the nucleic add injections; poorly defined FIA peaks were observed in the presence of phosphate, sodium lauryl sulfate and p-toluene sulfonate dopants. In general, different dopants resulted in different response patterns to the same nucleic acid. The nitrate counter ion yielded the highest sensitivity and a low noise level.

EXAMPLE 8

Using the methods of Example 5 and nucleic acids of Example 6, the influence of the electropolymerization time was examined by changing the number of cyclic voltammetric cycles between 5 and 15. The best performance was observed using 10 cycles.

EXAMPLE 9

Using the methods of example 5, the PPy/$NO_3^-$ film was deposited on a carbon paste electrode, yielding FIA nucleic acid detection signals similar to those described in Example 6. The carbon paste electrode (3 mm diameter, BAS) was made by mixing 3.25 g graphite powder and 1.75 g mineral oil, and the electrode surface smoothed on weighing paper.

EXAMPLE 10

Figure 7:
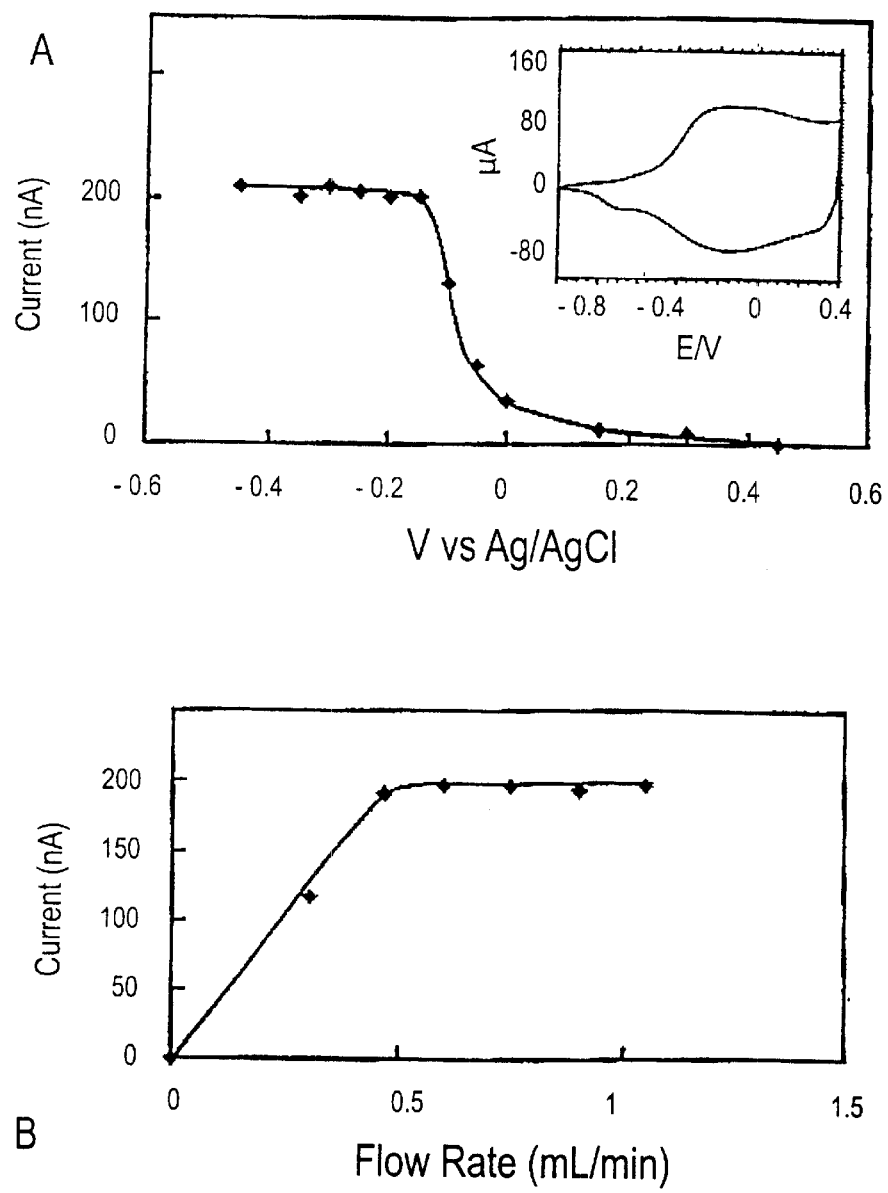
FIG. 7 depicts effect of the applied potential (A) and flow rate (B) upon the response of the PPy/$NO_3^-$-coated detector to injections of solutions of oligomers.

Using the methods of Example 5, the influence of the applied potential upon the flow-injection response of the PPy/$NO_3^-$ film was evaluated utilizing oligo(dA)$_{20}$. In FIG. 7A, the sigmoidal-shaped hydrodynamic voltammogram characterizes the relationship of the applied potential against the signal. The response started at potentials lower than +0.40 V, increased slowly between +0.40 V and 0.0 V, and increased more rapidly between 0.0 V and −0.15 V to reach a potential-independent plateau at lower potentials. Based on the cyclic voltammogram of the PPy/$NO_3^-$ electrode, shown in the inset in FIG. 7A, the PPy/$NO_3^-$ film is most redox active and conductive between 0.10 and −0.30 V. For obtaining the cyclic voltammogram, the PPy/$NO_3^-$ electrode was in a deaerated 0.1 M sodium-chloride electrolyte solution using a scan rate of 50 mV/s.

EXAMPLE 11

Using the methods of Example 5, the influence of flow rate upon the flow-injection response of the PPy/$NO_3^-$ film was evaluated utilizing oligo(dG)$_{20}$. As shown in FIG. 7B, the flow rate had a significant effect on the detector output. The response increased rapidly and linearly upon raising the flow rate between 0 and 0.48 mL/min and leveled off at higher rates, up to 1.1 mL/min.

EXAMPLE 12

Figure 8:
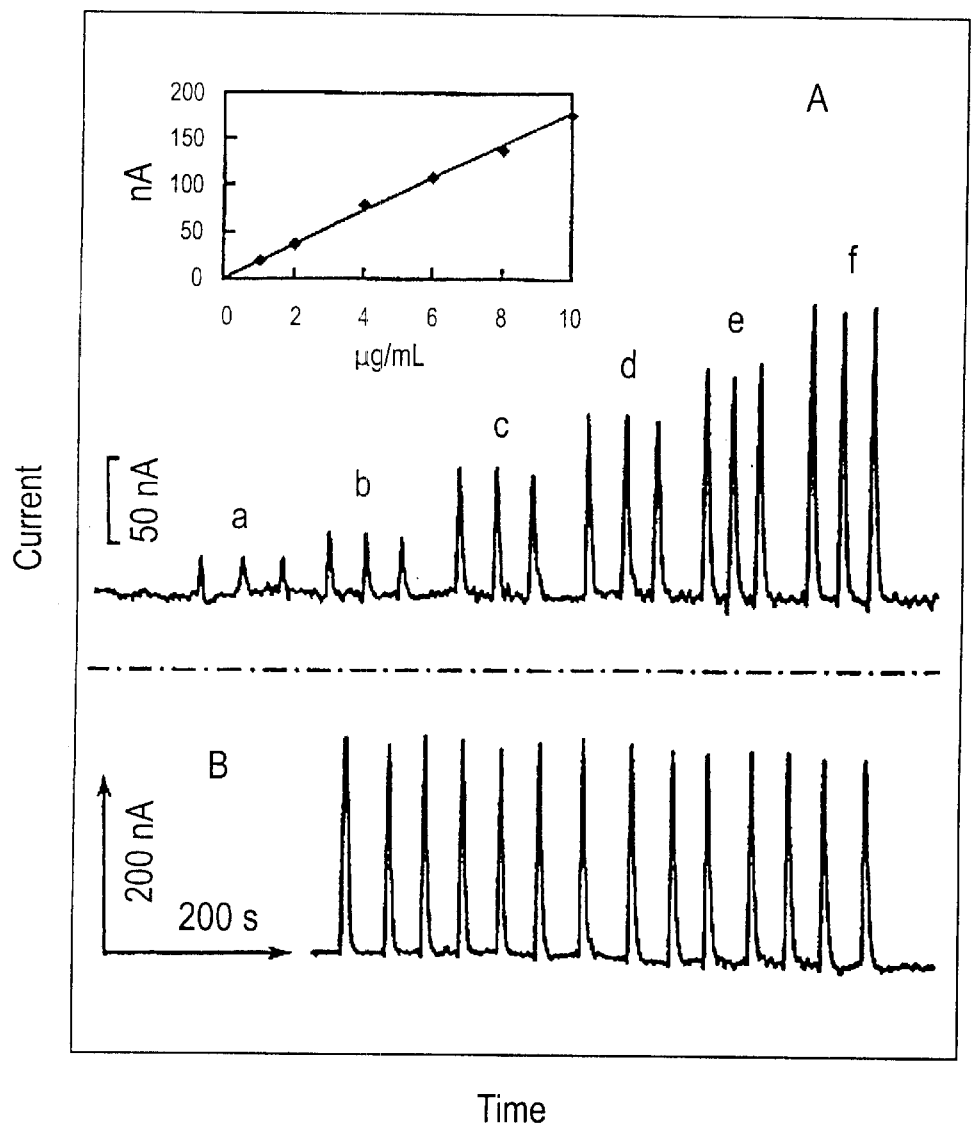
FIG. 8 depicts flow-injection detection peaks at the PPy-coated glassy-carbon electrode for (A) increasing concentrations of oligomers and (B) fourteen repetitive injections of a selected oligomer.

Using the methods of Example 5, the effects of increasing concentrations of a test nucleic acid were evaluated. Amperometric peaks were evaluated for increasing oligo (dT)$_{20}$ concentrations over a 1–10 μg/mL range, corresponding to 20–200 pg for the 20 μL injection loop utilized in the experiment. The results are shown in FIG. 8A. These data yielded a linear calibration plot, shown on the inset in FIG. 8A, the slope of which corresponded to a sensitivity of 17.8 nA. mL/μg with a correlation coefficient of 0.999. The estimated detection limit, based on the response to the 1 μg/mL solution, was at least 0.6 μg/mL ($9.4 \times 10^{-8}$ M), which corresponds to 12 ng for the 20 L injection volume. The concentration detection limit for the 20-kb dsDNA, 0.4 μg/ml ($3.1 \times 10^{-11}$ M), based on FIG. 6A (e), corresponded to $6.1 \times 10^{-16}$ M in the 20 L injection volume. Linearity was also observed utilizing injections of oligo(dA)$_{20}$ solutions of increasing concentration, of from 5–30 μg/L, and resulting in a slope of 18.8 nA. mL/μg.

EXAMPLE 13

Using the methods of Example 5, the precision of the response to a test nucleic acid was evaluated. A series of 14 successive injections of a 8 μg/mL oligo(dC)$_{20}$ solution was used to evaluate the precision of the response, with the results shown in FIG. 8B. A mean peak current of 240 nA and a relative standard deviation of 2.1% were obtained. A prolonged series of 30 repeated runs yielded a similar relative standard deviation.

EXAMPLE 14

Figure 9:
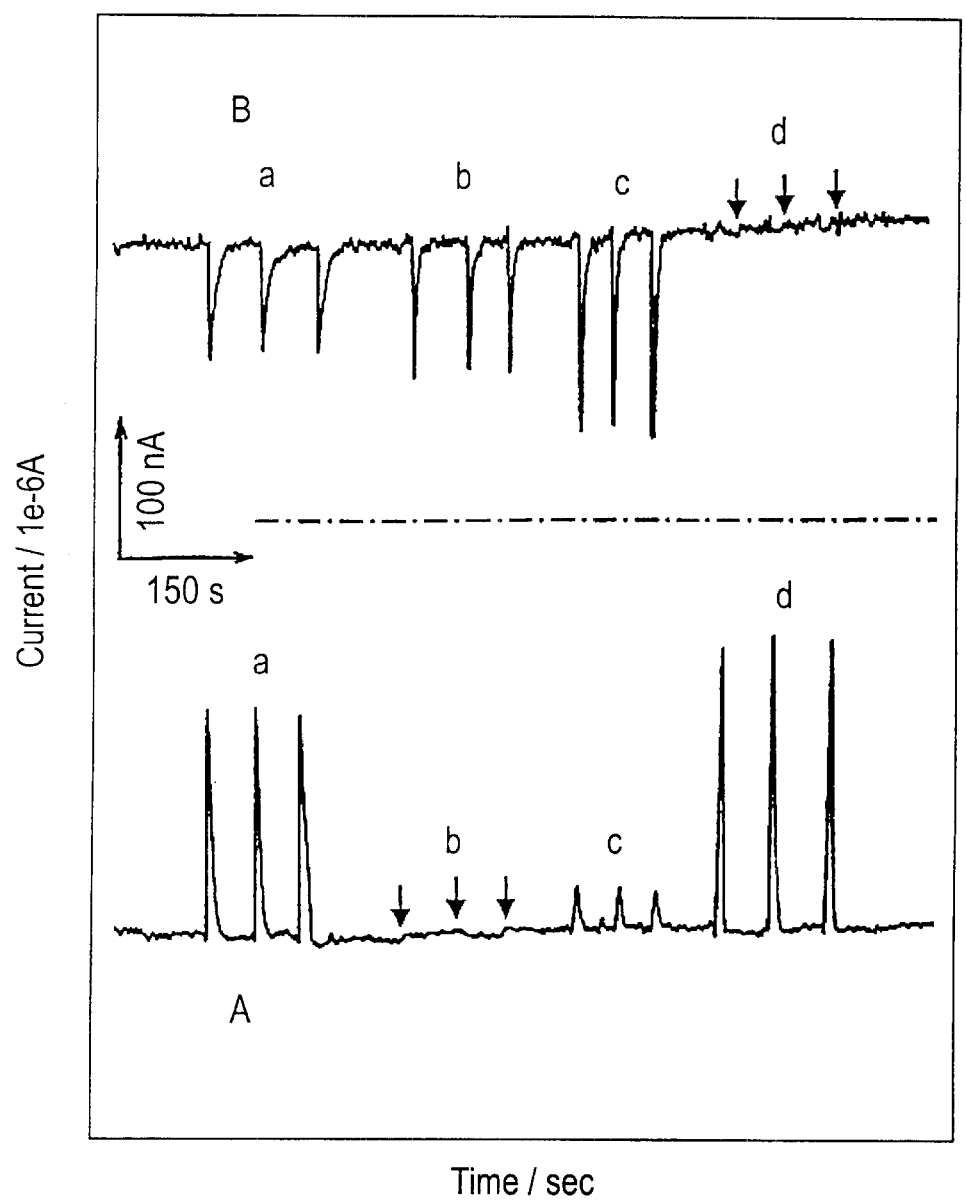
FIG. 9 depicts detection peaks at the PPy-coated glassy-carbon (A) and bare carbon-paste (B) electrodes to injections of various solutions.

Using the methods of Example 5, the susceptibility of the system to interference from oxidizable electroactive species, such as are frequently present in biological samples, was evaluated. Conventional amperometric detection of nucleic acids, based on the oxidation of the nucleobases or sugar backbone, are prone to interference from easily oxidizable electroactive species, such as ascorbic acid. As shown in FIG. 9, flow injection amperometric peaks for oligo(dG)$_{20}$ (a), ascorbic acid (b), acetaminophen (c), and oligo(dC)$_{20}$ (d) were obtained using a PPy/$NO_3^-$ electrode (A) and a bare carbon-paste electrode (B), operated at −0.15 V and +1.0 V, respectively. Injections of the oxidizable ascorbic acid and acetaminophen result in substantial anodic signals at the fairly high potential essential for the guanine oxidation at the bare carbon-paste electrode as shown in FIG. 8B. In contrast, the PPy/$NO_3^-$ electrode did not respond to ascorbic acid injections and yielded small acetaminophen peaks, substantially smaller than the oligonucleotide signals.

EXAMPLE 15

Figure 10:
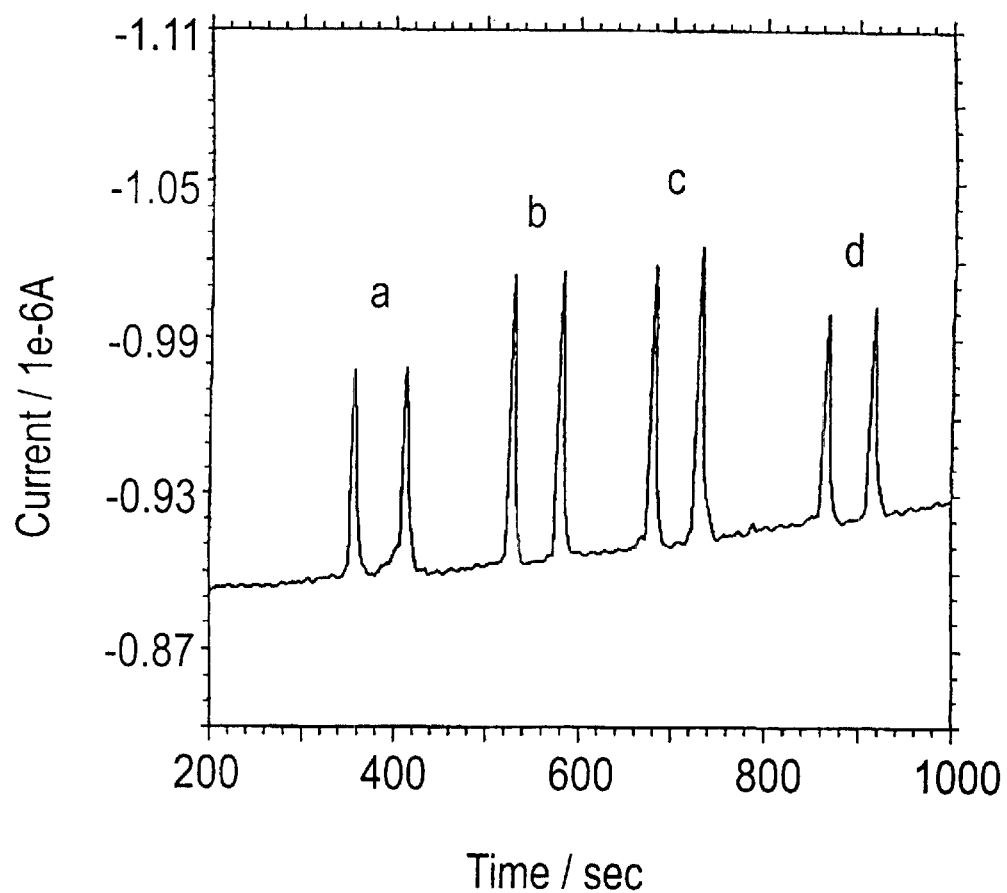
FIG. 10 depicts flow-injection amperometric peaks at the detector utilizing different oligomers.

Using the general methods of Example 5, a PPy film was prepared using a nucleic add as the sole dopant. The PPy/oligo(dG)$_{20}$ film was prepared using a 0.05 M pyrrole and 100 mg/L oligo(dG)$_{20}$ solution with 10 cyclic voltammetric cycles between 0.0 and +0.70 V at 50 mV/s. The coated electrode was thoroughly rinsed with water before use. FIG. 10 shows the flow injection amperometric peaks at the PPy/oligo(dG)$_{20}$-coated glassy-carbon electrode using oligo(dG)$_{20}$ (a), oligo(dT)$_{20}$ (b), oligo(dA)$_{20}$ (c), and a 12-mer oligonucleotide with sequence 5'-AGAGAGAGAGAG-3' (d) (SEQ ID NO: 2). The concentration of each nucleic acid was 10 μg/mL. Use of oligonucleotide dopants resulted in normal polymer growth and subsequent flow injection measurement of different nucleic acids.

EXAMPLE 16

A Maxtek Plating Monitor (Model PM-740, Maxtek Inc., Torrance, Calif.), interfaced with a personal computer was used in electrochemical quartz crystal microbalance (EQCM) experiments. This unit was used to drive the quartz crystal at its resonance frequency while displaying and recording the frequency response.

The QCM cell was obtained from Universal Sensors, Inc. (Metairie, La.), and was operated in its static/batch operation mode. The cell was connected to a frequency monitor, which was also combined with a CHI-620 Electrochemical Analyzer (CH Instruments, Austin, Tex.) that provided the potentiostatic control. International Crystal Manufacturing Co. (Oklahoma City, Okla.) provided T-cut quartz crystals with a fundamental resonance frequency (F0) of 5 MHz. These crystal wafers were loaded with gold-coated electrodes (area: 41 mm$^2$×2; thickness, 100 nm) formed by thermal evaporation of gold to a pre-deposited chromium underlayer on the quartz matrix. Contact of the crystals to both the oscillating circuit and the electrochemical circuitry was by using an HC-48 holder (ICM, Oklahoma City, Okla.). A platinum wire counter electrode and a Ag/AgCl (3 M NaCl) reference electrode (Model RE-1, BAS) completed the three-electrode electrochemical system.

Prior to use, the gold QCM wafers were ultrasonically cleaned by a 10-min exposure to a fresh Piranha solution. This was followed by ultrasonic rinsing with water and drying under nitrogen.

EXAMPLE 17

Voltammetric and EQCM experiments were conducted using the apparatus as described in Example 16 above. The crystal was immersed in a preparation solution containing pyrrole and the selected oligonucleotide as sole dopant or a blank deoxygenated 1 M sodium chloride. Oxygen removal was accomplished by bubbling high purity nitrogen for 20 minutes in the solution. The final volume of the test solution was 300 µL. The voltammetric scanning was initiated after approximately 10 minutes of frequency stabilization and the current and frequency outputs were monitored simultaneously. Typically ten voltammetric cycles were recorded. Repetitive measurements were performed by renewing the surface and repeating the above assay protocol. All experiments were conducted at room temperature.

Figure 11:
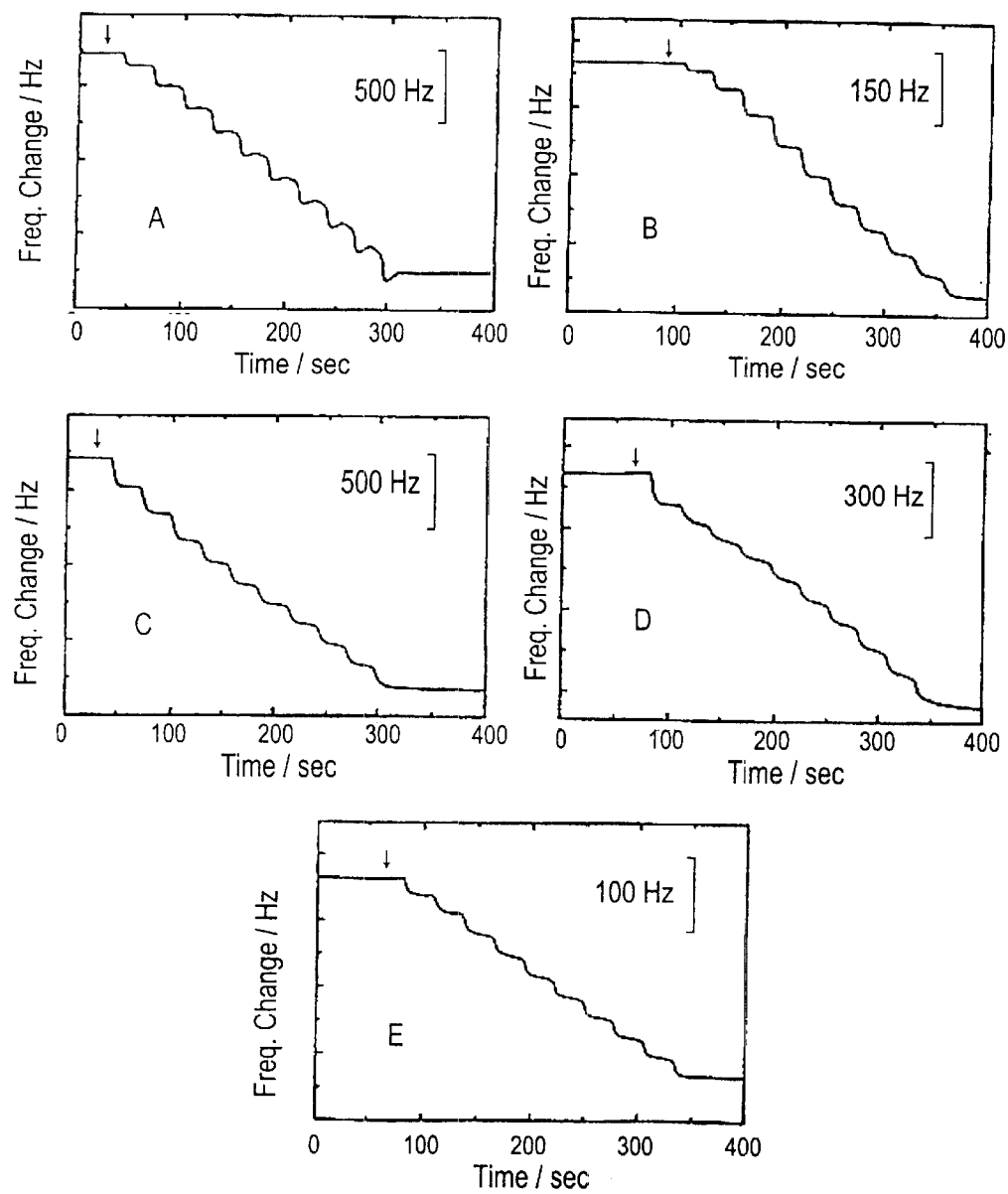
FIG. 11 depicts in situ electrochemical quartz crystal microbalance ("EQCM") response during electropolymeric growth of polypyrrole in the presence of different dopants.
Figure 12:
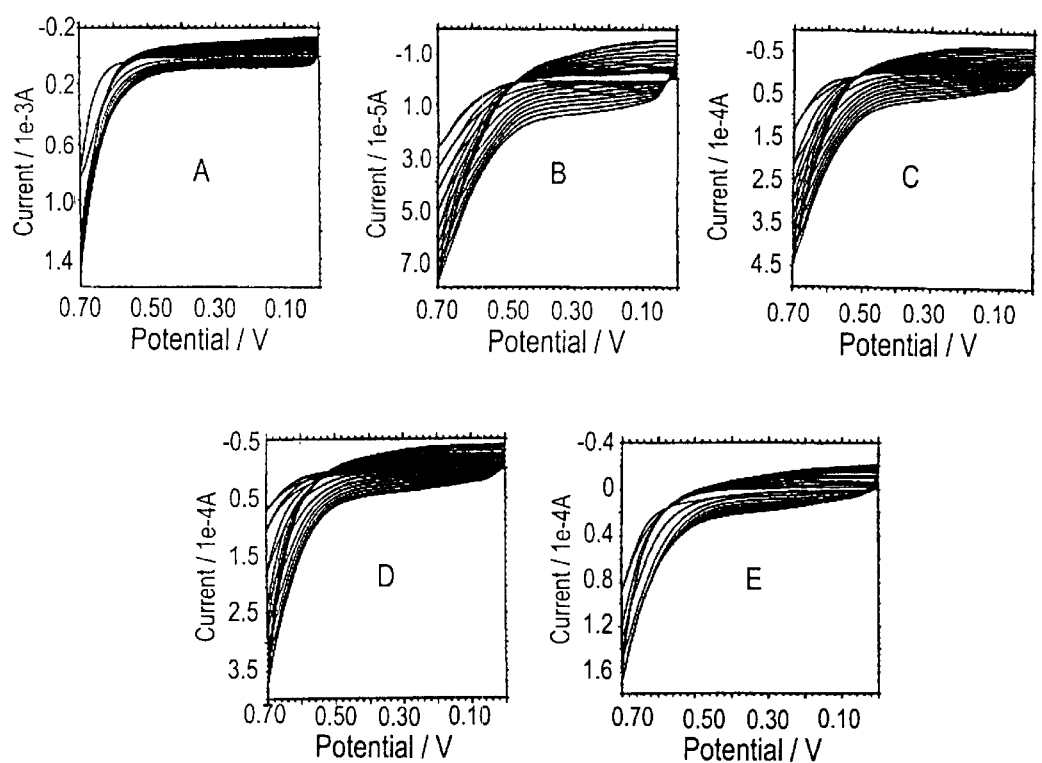
FIG. 12 depicts repetitive cyclic voltammograms recorded during the electropolymerization of polypyrrole in the presence of different dopants.

FIG. 11 shows typical time frequency QCM recordings obtained during the electropolymerization of PPy onto the gold surface in the presence of micromolar concentrations of the 8-mer (B), 20-mer (C), and 30-mer (D) oligonucleotides, as well as ssDNA (E) and sodium chloride (A). The corresponding cyclic voltammograms, over the 0.0 to +0.70V range, are shown in FIG. 12. In all cases, the QCM profiles displayed successive changes in the resonance frequency, corresponding to the individual potential cycles. Such frequency decreases reflected the increased mass associated with the growth of the PPy layer, and indicated a normal conducting polymer growth pattern during these potential sweeps. The sharp frequency decreases occurred primarily upon sweeping over the +0.55V–+0.70V–+0.55V potential range, where pyrrole oxidation takes place, with approximately a 5 second delay due to the relatively fast scan rate. The nearly linear decrease of the frequency with the sweeping time indicated that the film deposition occurred at a relatively fixed rate. Such growth profiles indicate that the anionic oligonucleotides, as well as ssDNA, are incorporated within the growing film for maintaining its electrical neutrality. Experimental results and analysis of QCM profiles demonstrated different frequency changes for different solutions, approximately 1482 Hz for Cl$^-$, 501 Hz for oligo(dG$_8$), 1520 Hz for oligo(dG$_{20}$), 851 Hz for oligo (dG$_{30}$), and 296 Hz for ssDNA. While the nucleic-acid doped films displayed a nearly steady-state frequency response at each potential cycle, growing peaks, demonstrated by intermittent frequency changes, were observed on the 'steps' of the PPy/Cl electrode (following the initial 3–4 potential sweeps). The later, observed also for PPy/NO$_3$ films, were attributed to the simultaneous anion doping/undoping process. No such peaks were observed for the PPy/nucleic add composites.

The cyclic voltammetric profiles of FIG. 12 revealed a normal polymer growth with increasing current upon repetitive scanning. Different electropolymerization growth rates were observed in different solutions. The oligo(dG$_{20}$) anion (C) displayed the largest growth current and frequency change among the three oligonucleotide dopants. The current and frequency signals observed in the presence of ssDNA are smaller than those of the three oligonucleotides, which may be due to the relative bulk of ssDNA, resulting in lack of facile entrapment within the PPy network. Extremely small current and frequency changes, approximately 48 Hz for 10 cycles, were observed using oligo(dG$_1$) The dopant concentrations required for oligonucleotides, approximately 1.5×10$^{-5}$ M, was significantly lower than the required for a Cl$^-$ dopant. Chloride concentrations higher than 10$^{-2}$ M were essential for producing good quality conducting films, as compared to micromolar levels for oligonucleotides.

EXAMPLE 18

Figure 13:
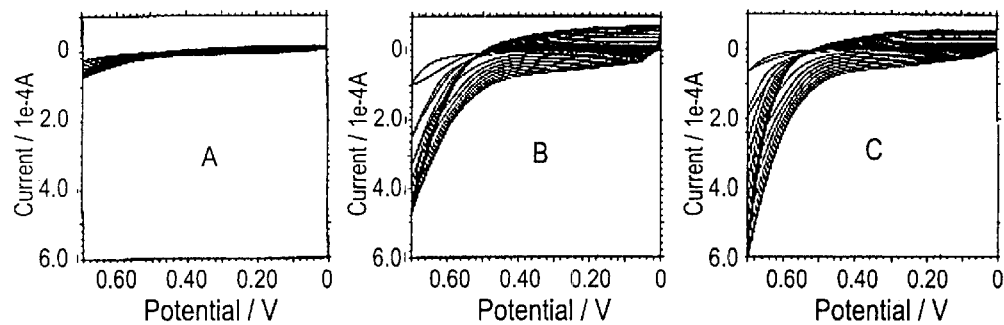
FIG. 13 depicts the effect of oligo($dG_8$) dopant concentration upon PPy growth.

Using the methods described in Example 16, the level of the nucleic acid dopant on the growth pattern of electropolymerized PPy was evaluated. FIG. 13 shows the voltammetric profiles for PPy growth in the presence of different oligo(dG$_8$) concentrations: 1.5×10$^{-5}$ M (A), 3×10$^{-5}$ M (B), and 4.5×10$^{-5}$ M (C). Limited electropolymerization was observed at the 1.5×10$^{-5}$ M oligo(dG$_8$) dopant level, while faster growth, with nearly 10-fold larger voltammetric currents, were observed for the higher oligo(dG$_8$) concentrations.

EXAMPLE 19

Figure 14:
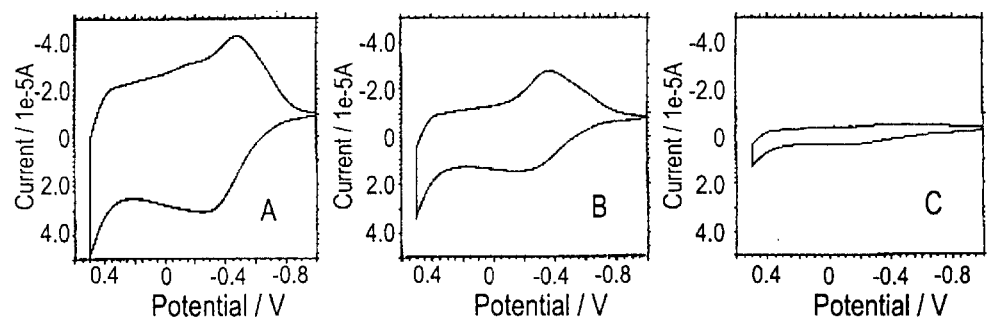
FIG. 14 depicts cyclic voltammograms at the PPy-coated electrodes in a 1M NaCl solution.

Using the methods of Example 16 the effect of the nucleic acid counter ion on the shape of the cyclic voltammogram in a blank electrolyte solution was evaluated. FIG. 14 shows cyclic voltammograms for the PPy/Cl (A), PPy/oligo(dG$_{20}$) (B), and PPy/ssDNA (C) modified electrodes in a 1M NaCl solution. The PPy/oligo(dG$_{20}$) film displayed redox response characteristics similar to those of PPy/Cl (B vs. A), with a wide conductive region, a cathodic peak around −0.37 V and an anodic peak at approximately −27 V; the corresponding PPy/Cl peak potentials are −0.45 and −0.31 V, respectively. The redox activity of both films started around −0.80 V. The total charge consumed within the conducting region of the PPy/oligo(dG$_{20}$) film was about half that of the PPy/Cl film. The redox activity was reduced considerably in the presence of ssDNA (C). The different cyclic voltammogram profiles of FIG. 14 demonstrate that uptake of nucleic adds by PPy permits differentiation between chromosomal DNA and short oligonucleotides.

EXAMPLE 20

Figure 15:
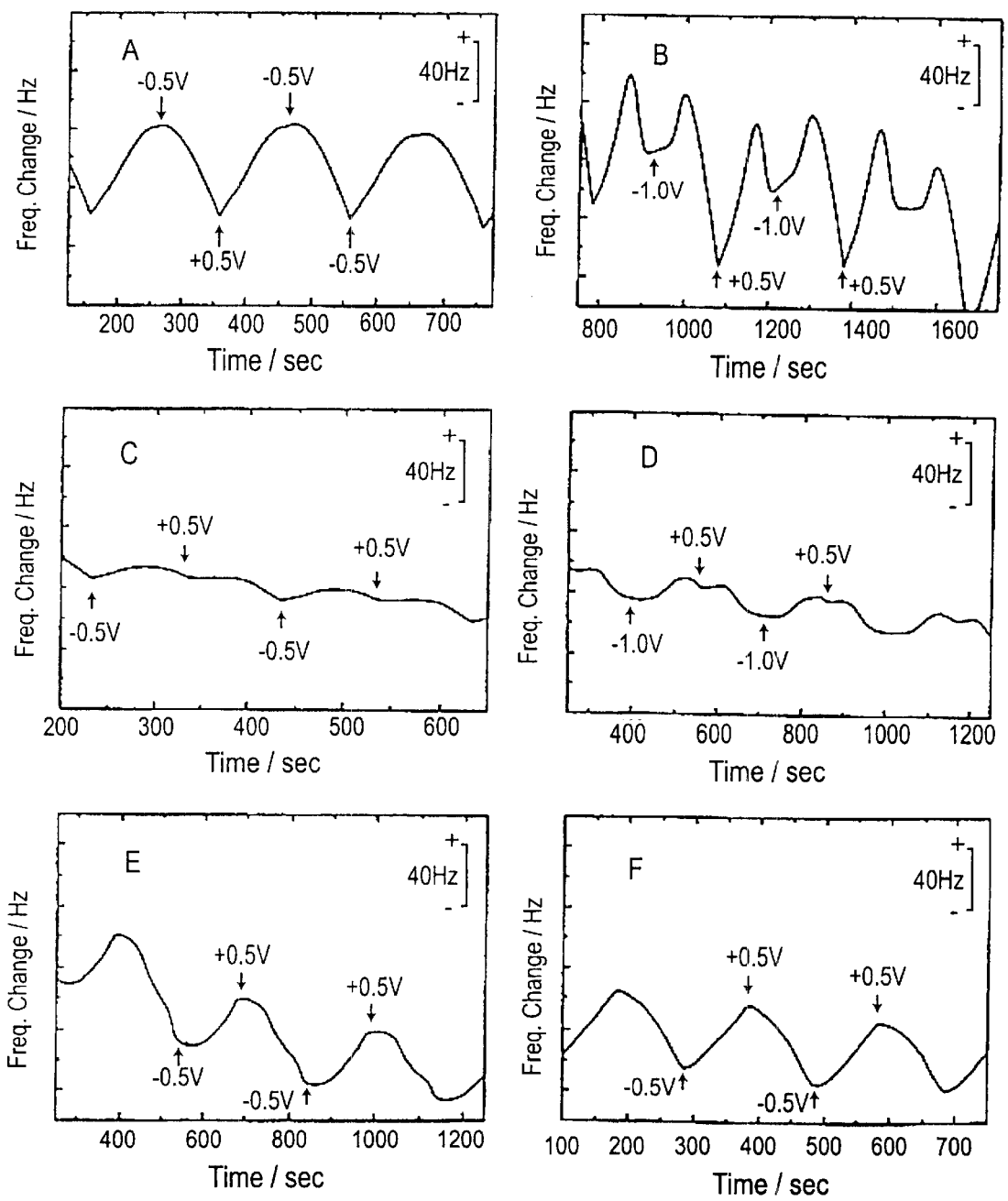
FIG. 15 depicts EQCM frequency response of PPy-coated electrodes during cyclic voltammetric scans over a voltage range using different dopants.

Using the general methods of Example 16, the ion-exchange processes of PPy/oligomer films were evaluated, particularly the ability to exchange the oligomer dopant with electrolyte anions. FIG. 15 illustrates QCM signals obtained for the PPy/Cl (A, B), PPy/oligo(dG$_8$) (C,D), and PPy/oligo (dG$_{20}$) (E,F) coated electrodes in 1M NaCl during potential sweeping over −0.5V to +0.5V (A, C, E) and −1.0 V to +0.5V (B, D, F) ranges. The PPy/Cl film and −0.5 V to +0.5 V scan revealed characteristic frequency decreases and increases, starting at −0.5 and +0.5 V, respectively, reflecting chloride movement in and out of the film during the PPy oxidation and reduction (A). A more complex ion-transport behavior was observed at the PPy/Cl electrode upon extending the potential scan to −1.0 V (B), including an additional frequency decrease and increase, starting at −0.48 V and −0.84 V, respectively, which appeared to correspond to a cation movement. The PPy/oligo(dG)$_8$ film displayed a limited ion-exchange activity over both potential ranges (C,D), with possible mixed ion-transport mechanism that becomes more pronounced upon extending the scan to the more negative potential. These profiles suggest a possible, albeit sluggish, movement of oligo(dG)$_8$ out of the PPy layer. In contrast, the PPy/oligo(dG$_{20}$) modified electrode exhibited an apparent cation-controlled transport mechanism, with a frequency rise during the oxidation and decrease upon reduction (E,F).

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

5. The apparatus of claim 1, wherein the free oligomer is an oligonucleotide comprising from about 8 to about 50 mers.

6. The apparatus of claim 1, further comprising:
means for accumulating a specimen on at least a portion of the polymer coated detection surface of the specimen electrode; and
means for amperometric detection of the specimen electrode upon accumulation of a specimen on at least a portion of the polymer coated detection surface of the specimen electrode.

7. The apparatus of claim 6, further comprising a reference electrode and means for determining the change in potential of the specimen electrode relative to the reference electrode upon accumulation of a specimen on at least a portion of the polymer coated detection surface of the specimen electrode.

8. An apparatus for detection of DNA hybridization, comprising:
a specimen electrode; and
a conducting polymer composition coating a portion of the specimen electrode thereby defining a detection surface, wherein the conducting polymer composition

What is claimed is:

1. An apparatus for detection of DNA hybridization, comprising:
a specimen electrode with a detection surface; and
a conducting polymer composition coating the detection surface of the specimen electrode, wherein the conducting polymer composition comprises a conducting polymer and an oligomer not conjugated or bonded, directly or through an intermediate, to the conducting polymer and complementary to the DNA sequence to be detected.

2. The apparatus of claim 1, wherein the specimen electrode is a carbon, metallic or metal-coated crystal electrode.

3. The apparatus of claim 1, wherein the conducting polymer comprises an electropolymerized substance.

4. The apparatus of claim 3, wherein the electropolymerized substance is polypyrrole, polythiophene, polyaniline or a derivative of any of the foregoing.

comprises a conducting polymer that is a member of the group consisting of polypyrrole, polythiophene, polyaniline and derivatives thereof and an oligomer not conjugated or bonded, directly or through an intermediate, to the conducting polymer and complementary to the DNA sequence to be detected.

9. The apparatus of claim 8, wherein the specimen electrode is a carbon, metallic or metal-coated crystal electrode.

10. The apparatus of claim 8, wherein the free oligomer is an oligonucleotide comprising from about 8 to about 50 mers.

11. The apparatus of claim 8, further comprising:
means for accumulating a specimen on at least a portion of the polymer coated detection surface of the specimen electrode; and
means for amperometric detection of the specimen electrode upon accumulation of a specimen on the polymer coated detection surface of the specimen electrode.

12. The apparatus of claim 11, further comprising a reference electrode and means for determining the change in potential of the specimen electrode relative to the reference electrode upon accumulation of a specimen on the polymer coated detection surface of the specimen electrode.

13. An apparatus for detection of nucleic acids in a flowing stream, comprising:

a first test electrode with a detection surface;

a conducting polymer containing a first anionic dopant not complementary to the nucleic acid to be detected coating at least a portion of the detection surface of the first test electrode;

means for providing electrical contact to the first test electrode;

means for flowing a liquid stream in contact with at least a portion of the detection surface of the first test electrode; and means for detecting nucleic acids in the flowing stream by amperometric detection of adsorption of nucleic acids onto the conducting polymer of the first test electrode.

14. The apparatus of claim 13 further comprising:

a reference electrode in contact with the liquid stream;

means for providing electrical contact to the reference electrode; and means for amperometric detection of the first test electrode relative to the reference electrode.

15. The apparatus of claim 13, wherein the conducting polymer comprises an electropolymerized substance.

16. The apparatus of claim 15, wherein the electropolymerized substance is polypyrrole, polythiophene, polyaniline or a derivative of any of the foregoing.

17. The apparatus of claim 13 wherein the first test electrode is a carbon, metallic or metal-coated crystal electrode.

18. The apparatus of claim 13, further comprising:

a second test electrode with a detection surface;

a conducting polymer containing a second anionic dopant coating at least a portion of the detection surface of the second test electrode;

means for providing electrical contact to the first test electrode;

means for flowing the stream in contact with at least a portion of the detection surface of the second test electrode; and means for detecting nucleic acids in the flowing stream by amperometric detection of absorption of nucleic acids onto the conducting polymer of the second test electrode.

19. The apparatus of claim 18 wherein the first dopant and the second dopant are different.

20. An apparatus for detection of nucleic acids in a flowing stream, comprising:

a first test electrode with a detection surface;

a conducting polymer composition, wherein the conducting polymer composition comprises a conducting polymer that is a member of the group consisting of polypyrrole, polythiophene, polyaniline and derivatives thereof, the conducting polymer composition containing a first anionic dopant not complementary to the nucleic acid to be detected and coating a portion of the first test electrode, thereby defining a detection surface;

means for providing electrical contact to the first test electrode;

means for flowing a liquid stream in contact with at least a portion of the detection surface of the first test electrode; and means for detecting nucleic acids in the flowing stream by amperometric detection of adsorption of nucleic acids onto the conducting polymer of the first test electrode.

21. The apparatus of claim 20 further comprising:

a reference electrode in contact with the liquid stream;

means for providing electrical contact to the reference electrode; and means for amperometric detection of the first test electrode relative to the reference electrode.

22. The apparatus of claim 20 wherein the first test electrode is a carbon, metallic or metal-coated crystal electrode.

23. The apparatus of claim 20, further comprising:

a second test electrode with a detection surface;

a conducting polymer composition, wherein the conducting polymer composition comprises a conducting polymer that is a member of the group consisting of polypyrrole, polythiophene, polyaniline and derivatives thereof, the conducting polymer composition containing a second anionic dopant and coating a portion of the second test electrode, thereby defining a detection surface;

means for providing electrical contact to the first test electrode;

means for flowing the stream in contact with at least a portion of the detection surface of the second test electrode; and means for detecting nucleic acids in the flowing stream by amperometric detection of absorption of nucleic acids onto the conducting polymer of the second test electrode.

24. The apparatus of claim 23 wherein the first dopant and the second dopant are different.

* * * * *